US010027362B2

(12) United States Patent
Liu et al.

(10) Patent No.: US 10,027,362 B2
(45) Date of Patent: Jul. 17, 2018

(54) WIRELESS WEARABLE BIG DATA BRAIN MACHINE INTERFACE

(71) Applicant: THE REGENTS OF THE UNIVERSITY OF CALIFORNIA, Oakland, CA (US)

(72) Inventors: Wentai Liu, Los Angeles, CA (US); Mau-Chung Frank Chang, Los Angeles, CA (US); Yen-Cheng Kuan, Los Angeles, CA (US); Yi-Kai Lo, Los Angeles, CA (US); Yan Zhao, Los Angeles, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 15/176,411

(22) Filed: Jun. 8, 2016

(65) Prior Publication Data

US 2016/0323000 A1 Nov. 3, 2016

Related U.S. Application Data

(63) Continuation of application No. PCT/US2014/070578, filed on Dec. 16, 2014.
(Continued)

(51) Int. Cl.
*H04B 7/00* (2006.01)
*H04B 1/3827* (2015.01)
(Continued)

(52) U.S. Cl.
CPC ............ *H04B 1/385* (2013.01); *A61B 5/0476* (2013.01); *A61B 5/7225* (2013.01); *G06F 3/015* (2013.01);
(Continued)

(58) Field of Classification Search
CPC .......... G06F 3/015; H02J 50/10; H04B 1/385; H04B 2001/3866; H04W 4/008; A61B 5/0476; A61B 5/7225
(Continued)

(56) References Cited

U.S. PATENT DOCUMENTS 6,230,049 B1 5/2001 Fischell et al.
2006/0058627 A1 3/2006 Flaherty et al.
(Continued)

OTHER PUBLICATIONS

Korean Intellectual Property Office (KIPO), International Search Report and Written Opinion, PCT/US2014/070578, dated Apr. 20, 2015, pp. 1-14, with claims searched, pp. 15-22.

*Primary Examiner* — Eugene Yun
(74) *Attorney, Agent, or Firm* — O'Banion & Ritchey LLP; John P. O'Banion

(57) ABSTRACT

A wireless wearable high data throughput (big data) brain machine interface apparatus is presented. An implanted recording and transmitting module collects neural data from a plurality of implanted electrodes and wirelessly transmits this over a short distance to a wearable (not implanted) receiving and forwarding module, which communicates the data over a wired communication to a mobile post processing device. The post processing device can send this neural data to an external display or computer enabled device for viewing and/or manipulation. High data throughput is supported by aggregating multiple groups of electrodes by multiple n-channel recording elements, which are multiplexed and then modulated into high frequency wireless communications to the wearable module. Embodiments include use of multiple radiators (multiple polarizations and/or spatially distributed), with beam alignment adjustment.

23 Claims, 20 Drawing Sheets

Related U.S. Application Data

(60) Provisional application No. 61/924,737, filed on Jan. 8, 2014, provisional application No. 61/916,512, filed on Dec. 16, 2013.

(51) Int. Cl.
| | |
|---|---|
| *A61B 5/0476* | (2006.01) |
| *G06F 3/01* | (2006.01) |
| *A61B 5/00* | (2006.01) |
| *H02J 50/10* | (2016.01) |
| *H04L 5/00* | (2006.01) |
| *H04W 4/80* | (2018.01) |

(52) U.S. Cl.
CPC ............ *H02J 50/10* (2016.02); *H04L 5/0044* (2013.01); *H04W 4/80* (2018.02); *H04B 2001/3866* (2013.01)

(58) Field of Classification Search
USPC ....................................................... 455/41.2
See application file for complete search history.

(56) References Cited

U.S. PATENT DOCUMENTS

| | | |
|---|---|---|
| 2006/0089112 A1 | 4/2006 | Irazoqui-Pastor et al. |
| 2008/0294033 A1 | 11/2008 | Yamazaki |
| 2012/0302858 A1 | 11/2012 | Kidmose et al. |

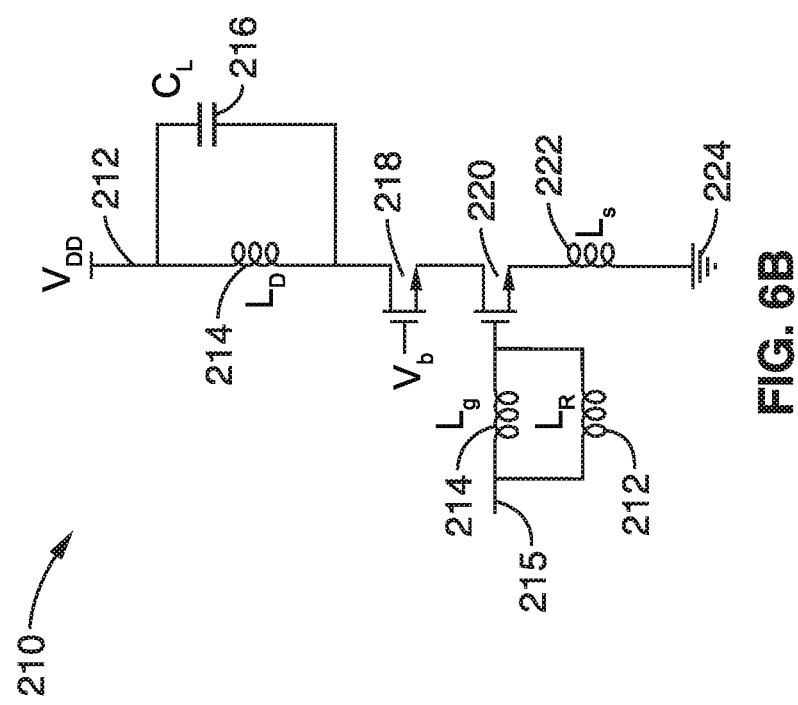

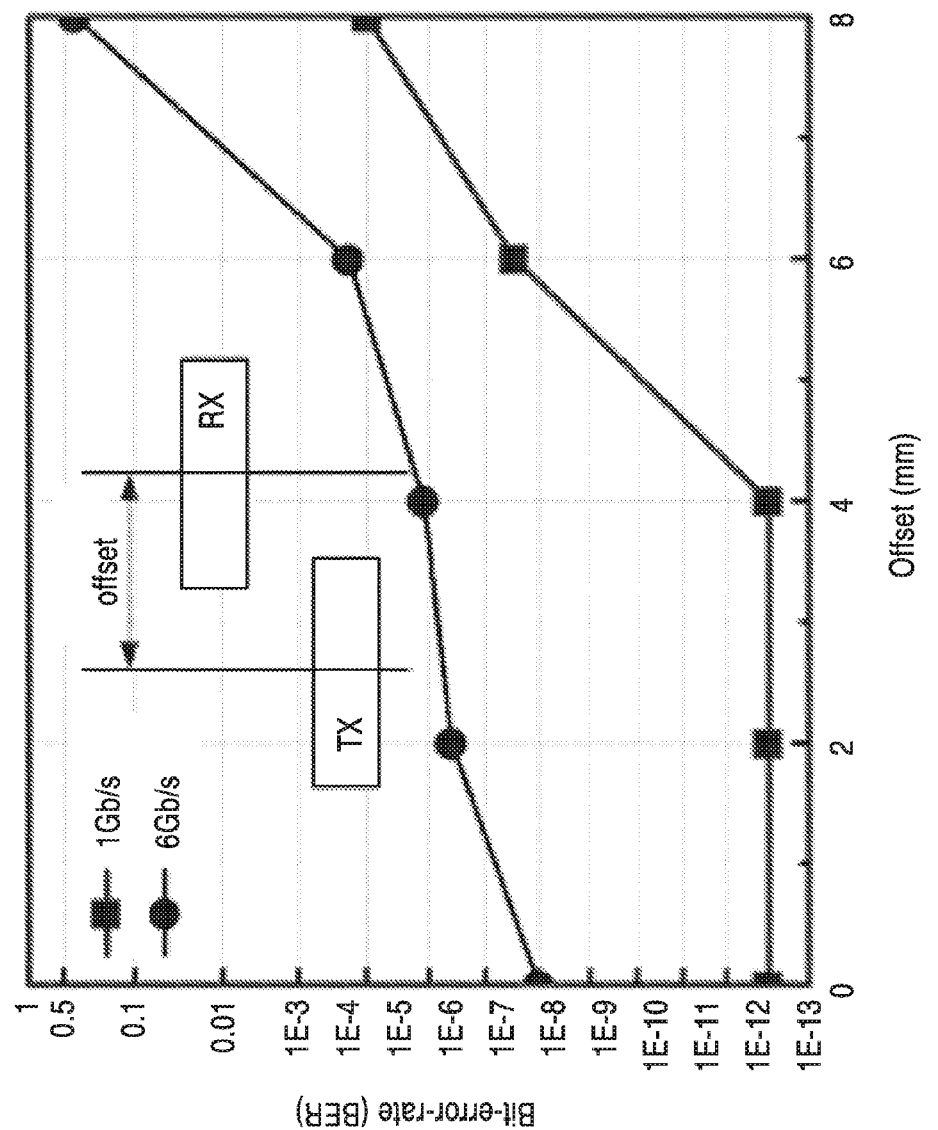

WIRELESS WEARABLE BIG DATA BRAIN MACHINE INTERFACE

CROSS-REFERENCE TO RELATED APPLICATIONS

This application is a 35 U.S.C. § 111(a) continuation of PCT international application number PCT/US2014/070578 filed on Dec. 16, 2014, incorporated herein by reference in its entirety, which claims priority to, and the benefit of, U.S. provisional patent application Ser. No. 61/924,737 filed on Jan. 8, 2014, incorporated herein by reference in its entirety, and also claims priority to, and the benefit of, U.S. provisional patent application Ser. No. 61/916,512 filed on Dec. 16, 2013, incorporated herein by reference in its entirety. Priority is claimed to each of the foregoing applications.

The above-referenced PCT international application was published as PCT International Publication No. WO 2015/095182 on Jun. 25, 2015, which publication is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technological Field

This technical disclosure pertains generally to machine interfaces, and more particularly to a brain to machine interface.

2. Background Discussion

Existing brain machine interface (BMI) systems are capable of supporting only a few mega-bit/s (<10 Mb/s) data rate for transferring monitored/recorded brain neural data, and most of the systems transfer the data to a remote terminal through wire-only interfaces. This low rate of data transfer (small data) and spatial/mobility limitation, as constrained by the physical wires, limits the feasibility of investigating brain activities in a large-scale and fine-resolution view, while also limiting the freedom of movement of the monitored patient/subject.

Accordingly, a need exists for a big (large) data brain to machine interface which is mobile and readily implemented.

BRIEF SUMMARY

A user-friendly brain machine interface (BMI) system is presented which can monitor/record a large amount ("big data") of brain neural activities of a human/animal based on input from a plurality of electrodes implanted on the cranium (braincase) of the patient. The BMI system collects the neural data from these electrodes, performs signal processing/analysis on that neural data, and transfers wirelessly those processed/raw data to a remote terminal through an implant recording-and-transmitting module to a wearable receiving-and-forwarding module, and out to a mobile post-processing unit. The disclosed BMI system can support researchers and applications for investigating brain activity mapping, diagnosing brain abnormalities, and developing new technologies or treatments to prevent or cure brain-related illness.

One important element of the disclosed BMI system, is that it partitions the data transfer medium into three sections, which are (1) short-distance wireless communication, (2) low-complexity (e.g., 5 wires only) wire communication, and (3) local area/infrastructure wireless communication. The supporting modules/devices for each section are implemented in either an implantable or wearable format.

Through such partitioning architecture, the disclosed BMI system allows transferring large amounts of monitored/recorded brain neural data (big data) at a rate of at least a giga-bit per second (1+ Gb/s) to a remote terminal, meanwhile still allowing or enabling the patient/subject to move freely.

In the disclosed BMI system, the recording-and-transmitting module and the receiving-and-forwarding module can be implemented through system-in-a-package (SiP) or system-on-a-chip (SoC) technologies. The mobile post-processing module can be readily realized through utilizing an existing smartphone or embedded computer platform configured with customized software for processing the monitored/recorded brain data. The adapter connecting the receiving-and-forwarding module and the mobile post-processing module can be implemented with commercial off-the-shelf (COTS) chips on a PCB board, or using any desired level of integration in the fabrication of the electronics.

Further aspects of the presented technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The disclosed technology will be more fully understood by reference to the following drawings which are for illustrative purposes only:

FIG. 6B is a schematic of an amplifier circuit for use in FIG. 6A, which utilizes an inductor as the receiving radiator element according to at least one embodiment of the present disclosure.

FIG. 16 is a bit-error-rate (BER) plot depicting performance degradation in response to misalignment according to at least one embodiment of the present disclosure.

DETAILED DESCRIPTION

An apparatus and method are disclosed for a wireless wearable big-data brain machine interface (W2b2/Wwbb).

Figure 1A:
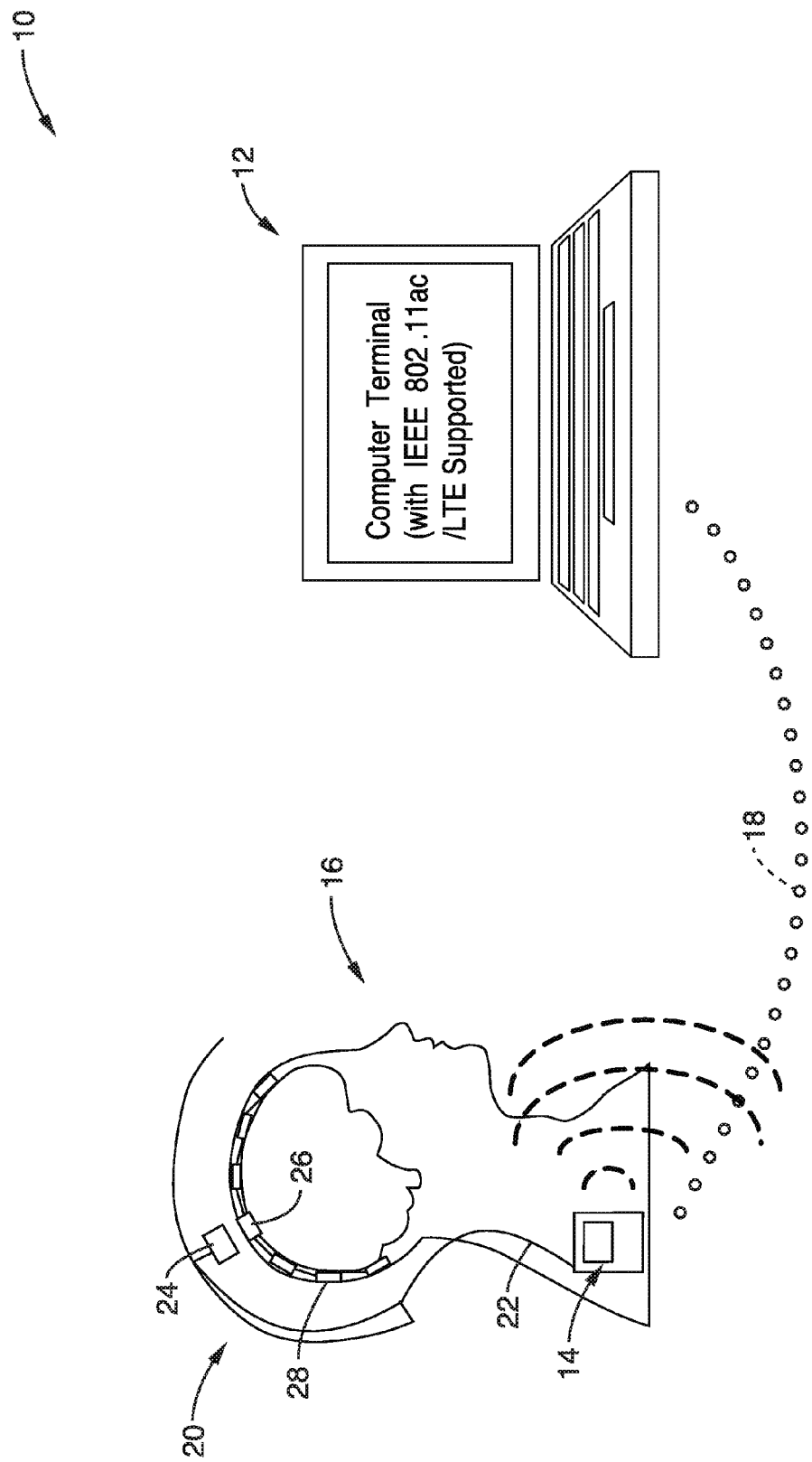
FIG. 1A through FIG. 1C are block diagrams of a big data brain machine interface (BMI) according to at least one embodiment of the present disclosure.
Figure 1B:
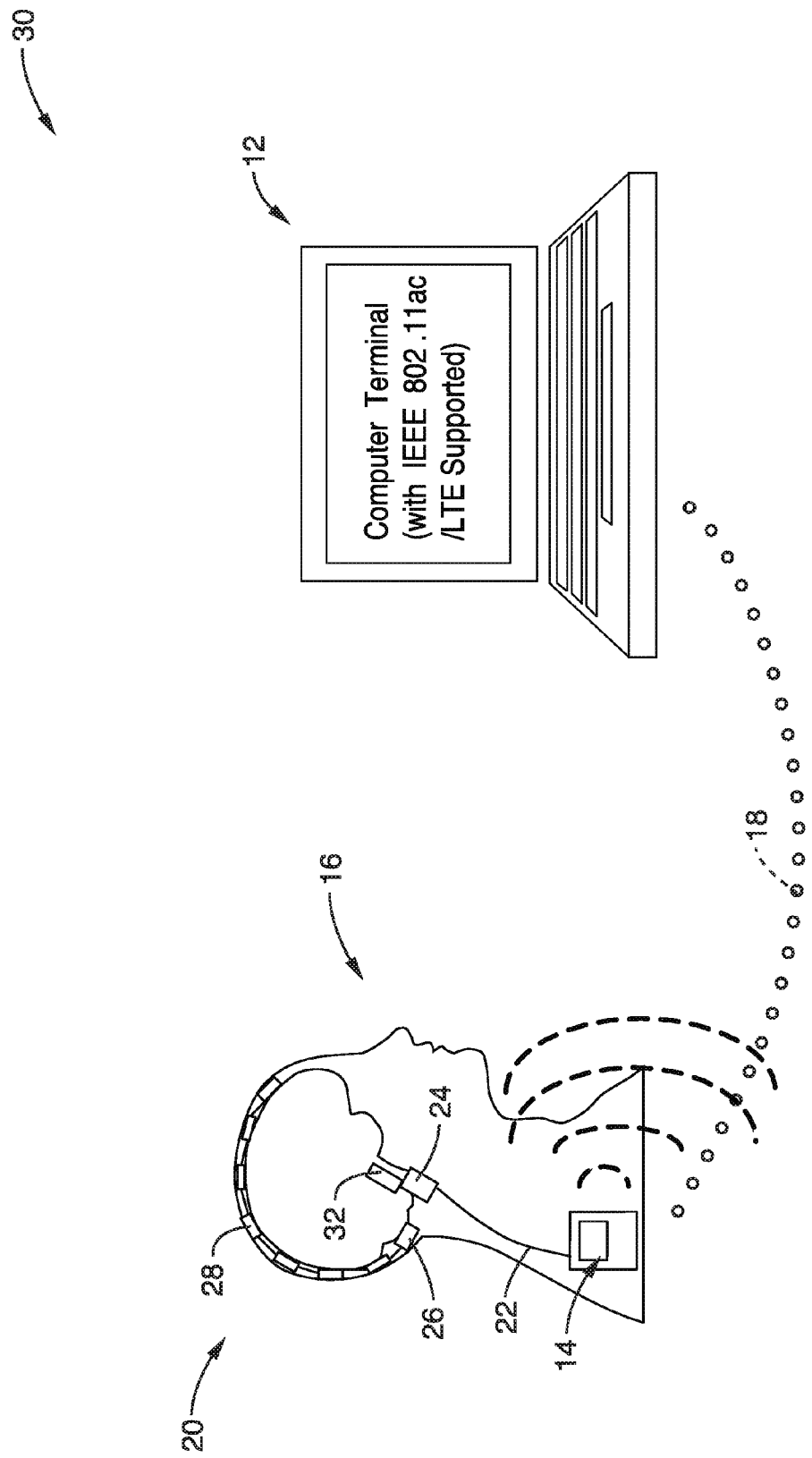
Figure 1C:
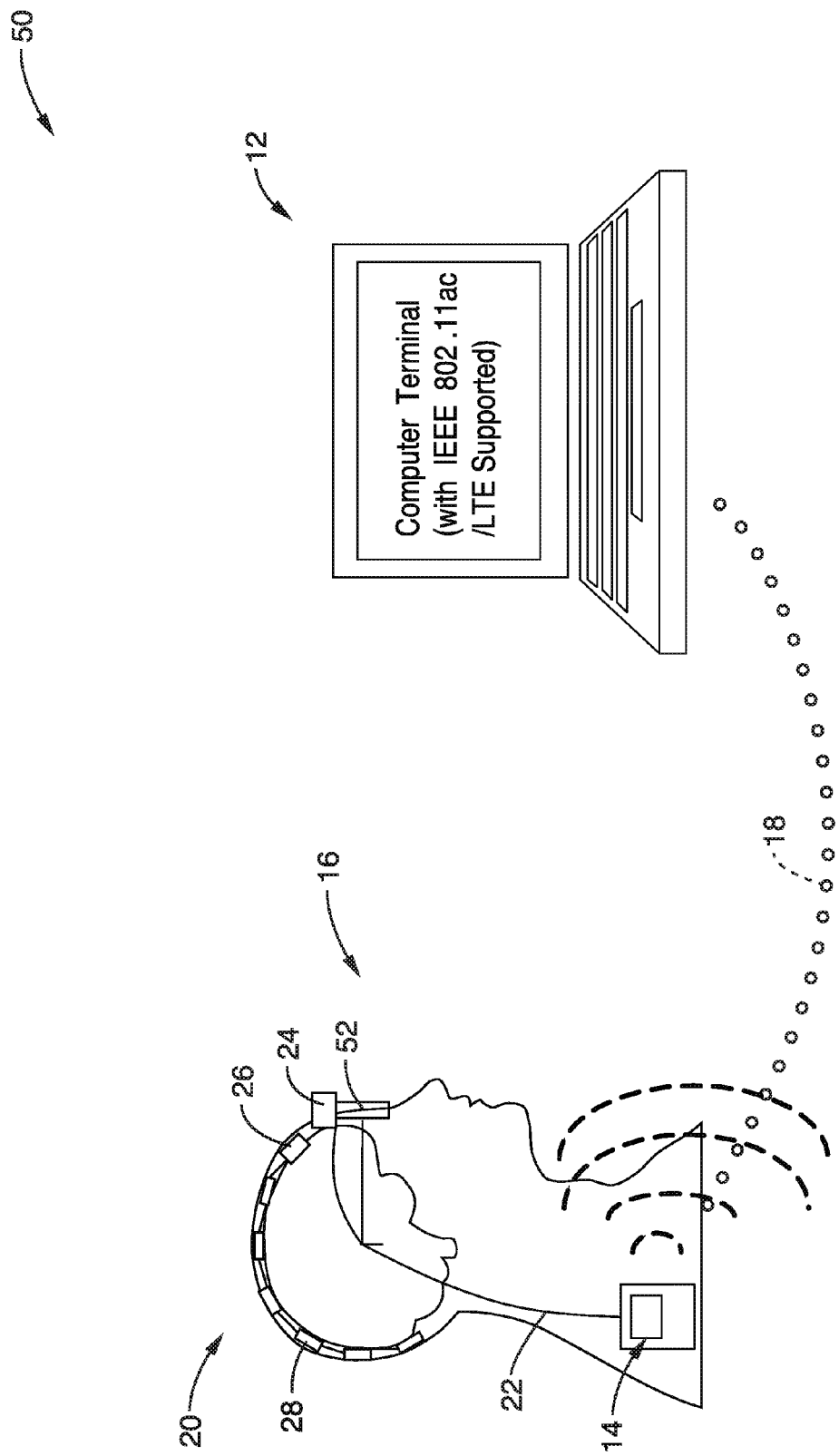

FIG. 1A through FIG. 1C depict different general example embodiments 10, 30, 50 of a brain-machine interface (BMI) system which is configured for supporting giga-bit/second wireless data transfers, while enabling the subject/patient to move freely and overcome the spatial limitations existing in conventional BMIs. In addition, the system is configured for being readily implemented by custom programming an existing mobile device (e.g., smart phone), as a post-processing and/or communication intermediary, of the brain data being registered by the device.

Each of these embodiments relies upon a plurality of implanted electrodes 28 (i.e., implanted in the scalp on cranial regions of a patient), an implanted recording-and-transmitting module 26, a wearable receiving-and-forwarding module 24 whose output is exemplified with a wired power and communication connection 22 to a mobile post-processing module 14, shown in relation to a BMI user/patient 16. The BMI system is configured for communicating wirelessly with external devices 12, such as a computer enabled electronic device (e.g., laptop, tablet, palmtop, smart phone, personal computer and so forth).

The BMI system is shown implementing the wearable receiving-and-forwarding module 24 within a wearable head covering 20 (e.g., hat) in FIG. 1A, in a headset 32 in FIG. 1B, and in a set of glasses 52 in FIG. 1C. It should be appreciated that these mechanisms for retaining the receiving-and-forwarding module proximal the cranial regions of the patient/user, are shown by way of example and not limitation, as other retention mechanisms may be utilized and combinations thereof without limitation. It will also be noted that since the receiving-and-forwarding module 24 must be retained in sufficient proximity to recording-and-transmitting module 26, the positioning of these modules are interdependent.

The implant and wearable modules establish a short-distance (approximately 1 cm) wireless link at greater than 5 GHz bands (including millimeter wave (mmWave) frequency bands). Through this wireless link, the under-skin recorded brain neural data from inside the brain is delivered to its exterior, by the BMI system. The wearable receiving module 24 forwards the received neural data to the mobile module 14 (e.g., smart phone running (executing) BMI application programming) exemplified as connected through a wired interface 22. The mobile module can further process the neural data (e.g. feature extraction, compression, etc.), and/or transfer the processed/raw data to a remote terminal through wireless local area networks (e.g., IEEE 802.11 a/b/c/n etc.) or cellular networks (e.g., 3G, 4G LTE, etc.), or other communication media and protocols as desired. As shown in these figures, the wearable receiving-and-forwarding module can be attached to devices (e.g., hat, headset, glasses, and so forth) at various places proximal cranial regions according to the locations of the implant recording-and-transmitting module.

Figure 2:
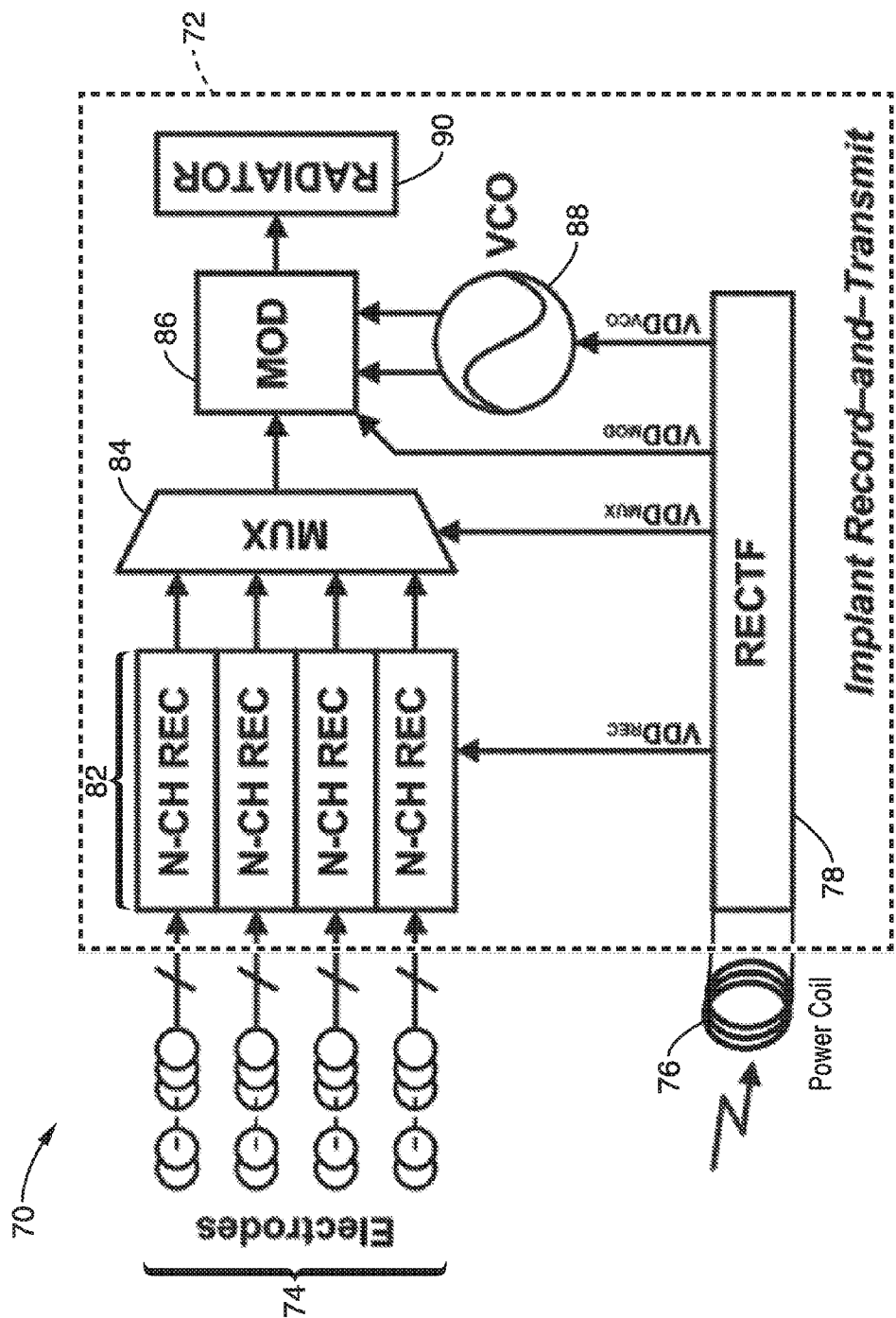
FIG. 2 is a block diagram for an implantable record-and-transmit module according to at least one embodiment of the present disclosure.

FIG. 2 illustrates an example of implant recording and transmitting 70, utilizing an implanted recording-and-transmitting module 72 shown receiving inputs from multiple electrodes 74, and receiving power through an inductive power coil 76, or other known means for wirelessly coupling power to the implant. Within the module are seen multiple neural recorders (REC) 82 which each are configured to connect to multiple electrodes within the plurality of electrodes 74. It should be appreciated that the neural recorders can be implemented in a number of different ways without departing from the teachings of the present disclosure. In at least one embodiment, these neural recorders sample the neural signals at a desired sampling rate and convert the neural levels to a digital signal (e.g., utilizing analog-to-digital converters (ADCs)). Various digital approaches can be utilized for generating digital signals corresponding to the analog output from the neural electrodes. It should even be appreciated that embodiments of the present disclosure can be implemented in which analog signals themselves are utilized as a modulation input for a transmitter, and demodulated in a receiver.

The recording circuits 82 generate digitized recording outputs to a multiplexer (MUX) (or serializer) 84, which aggregates the digitized outputs of the multiple recorders into a single bit-stream into a modulator (MOD) 86. The modulator receives a carrier wave, shown from a voltage controlled oscillator (VCO) 88, which is modulated by a baseband signal from the output of multiplexer (MUX) 84 to output a radio frequency signal into radiator (RAD) 90. It will be appreciated that alternate embodiments are discussed later which can utilize multiple multiplexers and modulators for creating signal streams and encoding of those signal streams onto the available wireless channels supported. It should be appreciated that radiator (RAD) 90 radiates the modulated output from the implant module through medium, such as skin, air, and so forth. The radiator can be implemented in various forms, including but not limited to an on-chip inductor, on-chip capacitor, on/off-chip antenna, or other structure configured for radiating a signal at the carrier frequency, and depending on the allowable link margin, given power and/or area constraints.

A power circuit 78, herein referred to as a rectifier (RECTF), is configured to receive wireless power from the attached power coil 76, based on inductive coupling from a proximally-located driven power coil in the wearable receive-and-forward module. The received power is optionally converted or regulated, then bussed to supply power to supply the various active circuits, such as RECs, MUX, MOD, and VCO, in the implanted device, with these voltages being exemplified as $VDD_{REC}$, $VDD_{MUX}$, $VDD_{MOD}$, $VDD_{VCO}$.

Figure 3:
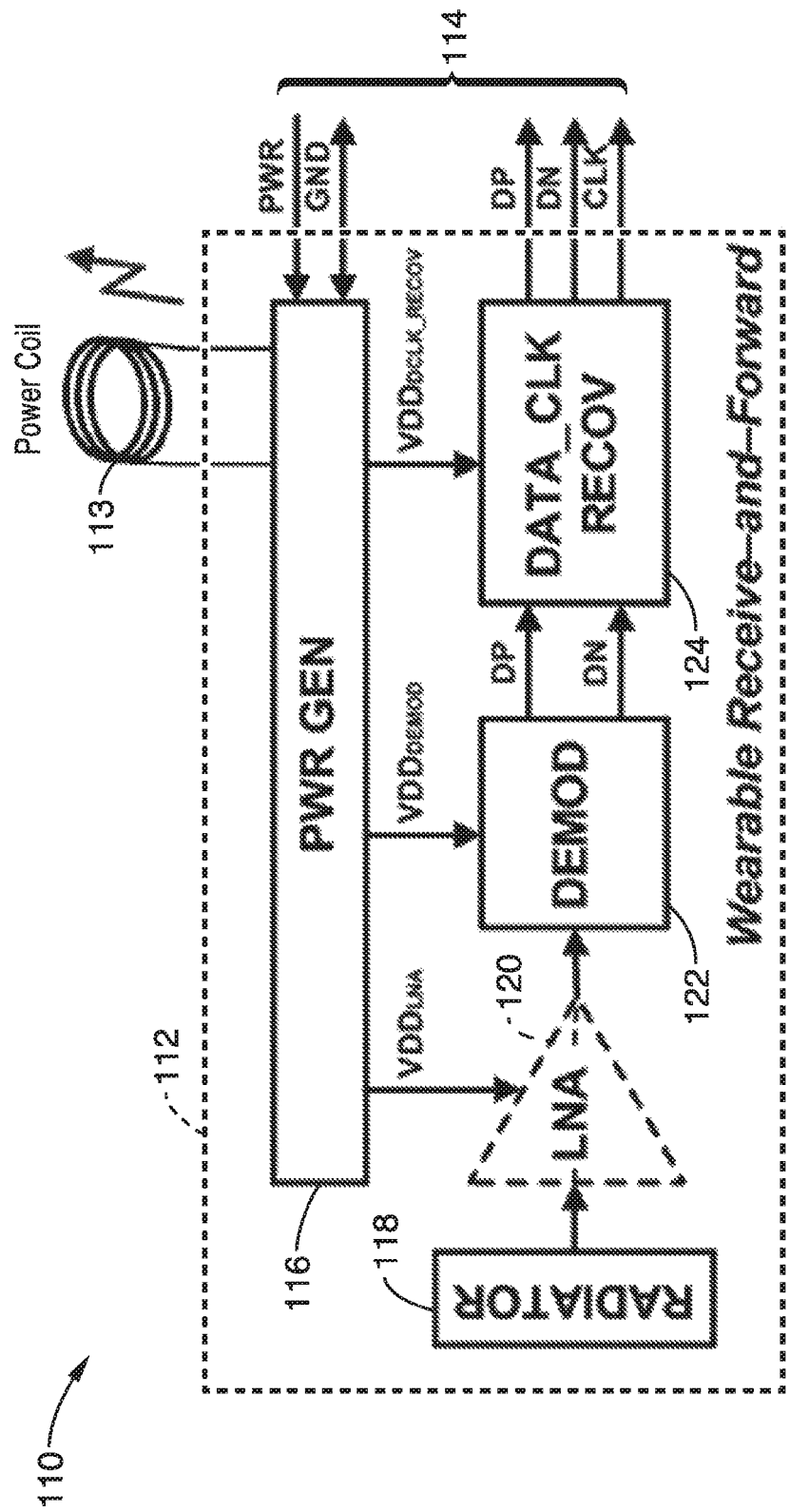
FIG. 3 is a block diagram for a wearable receive-and-forward module according to at least one embodiment of the present disclosure.

FIG. 3 illustrates an example embodiment of receiving and forwarding 110 utilizing a wearable receiving-and-forwarding module 112 coupled to a power coil 113 and having input/output signals 114. An inductive power generator circuit 116 is seen which receives power (e.g., PWR and GND) which is converted to proper voltages as necessary to supply its own circuitry, through supplies $VDD_{LNA}$, $VDD_{DEMOD}$, $VDD_{DCLK\_RECOV}$. In addition, power generator 116 drives a power coil 113 for inductive power coupling to the implant record-and-transmit circuit seen in FIG. 2. A modulated radio-frequency is received from the implant module in receive-and-forward module 112 on radiator (RAD) 118, after which the signal may be optionally amplified, such as by a low-noise amplifier (LNA) 120. The modulated radio-frequency signals are then demodulated by demodulator (DEMOD) 122 to extract the baseband signal received from the implant module. Demodulated output is shown as a differential signal data_positive (DP), and data_negative (DN), which are received at a data block recovery circuit 124 that operates to extract a clock signal from the differential data signal and output the differential data (DP, DN) and a clock (CLK) signal. The extracted baseband signal is in the form of a digital neural data bit-stream that is at (significantly) lower symbol rate than the carrier frequency which preferably exceeds approximately 5 GHz, including millimeter wave frequency bands.

It will be appreciated that in alternate embodiments, demodulator 122 can be configured to output a single-ended output, which would then be preferably converted at the clock recovery circuit to a differential output to increase robustness of signal communication, and to overcome any signal integrity issues of wire data transfer/forwarding.

Figure 4:
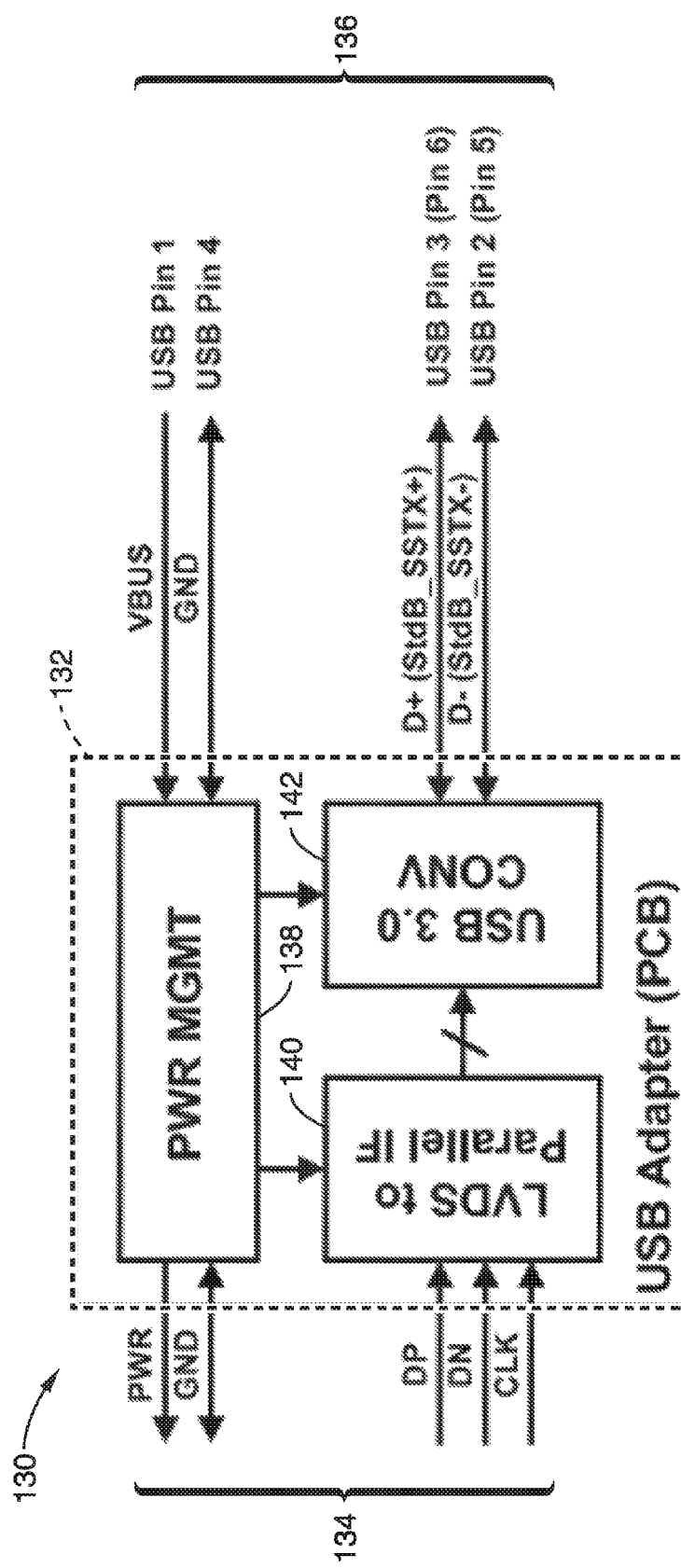
FIG. 4 is a block diagram for an adapter module to change digital data formatting according to at least one embodiment of the present disclosure.

FIG. 4 illustrates an example embodiment of converting 130 signal types using a communications adapter 132 configured for converting signals 134 generated by the receive-and-forward module of FIG. 3 to an output 136 which is in a format that is more readily utilized in communicating with a mobile post processing module. Although a mobile post processing module can be implemented according to the present disclosure to read data in the format provided by the wearable receive-and-forward module, this may be less preferred as it would involve designing a custom processor based electronic device for receiving and processing these signals. Using the interface of FIG. 4, the simple signaling system of FIG. 3 is adapted into a robust communication protocol which can be utilized to communicate with off-the shelf processor-enabled electronic devices upon which BMI application programming has been loaded to process the neural data and optionally communicate it (e.g., wirelessly) to a display, network, computer system or the like for viewing, storing, and/or manipulating. By way of example and not limitation, this example receives five-wire interface signals (PWR, GND, DP, DN, and CLK) from receive-and-forward module 110 of FIG. 3 which are converted by this adapter into a universal serial bus (USB) format. Although other intermediary communication protocols could be utilized with the present disclosure, it will be appreciated that a wide range of devices, including smart phones, support USB communications, and have at least one USB port.

Adapter 132 is shown with a power management (PWR MGMT) 138 circuit that receives power from the USB (VBUS pin), shown coming in as VBUS and GND, and generates the required powers for adapter circuits, and for outputting power (PWR, GND) as utilized by wearable module 110 of FIG. 3.

It will be appreciated that a communications adapter, such as exemplified in FIG. 4, may be integrated within the circuitry of the wearable receive-and-forward module, or it may be otherwise coupled to that circuitry. Alternatively, the adapter may be configured for attachment to the mobile post processing module, although for the majority of applications this may be less preferred, as the simple native communications protocol from the wearable receive-and-forward module is then utilized across the distance between the devices increasing the possibility of signal degradation/error.

Signals from the wearable module are exemplified as being processed in a low-voltage differential signal to parallel single-ended interface (LVDS to Parallel IF) 140 that converts the high-speed differential signals-DP and DN into low-speed parallel single-ended signals to a USB converter 142 that translates the converted parallel single-ended signals into the differential signals D+ and D− according to USB standards/protocols.

Figure 5A:
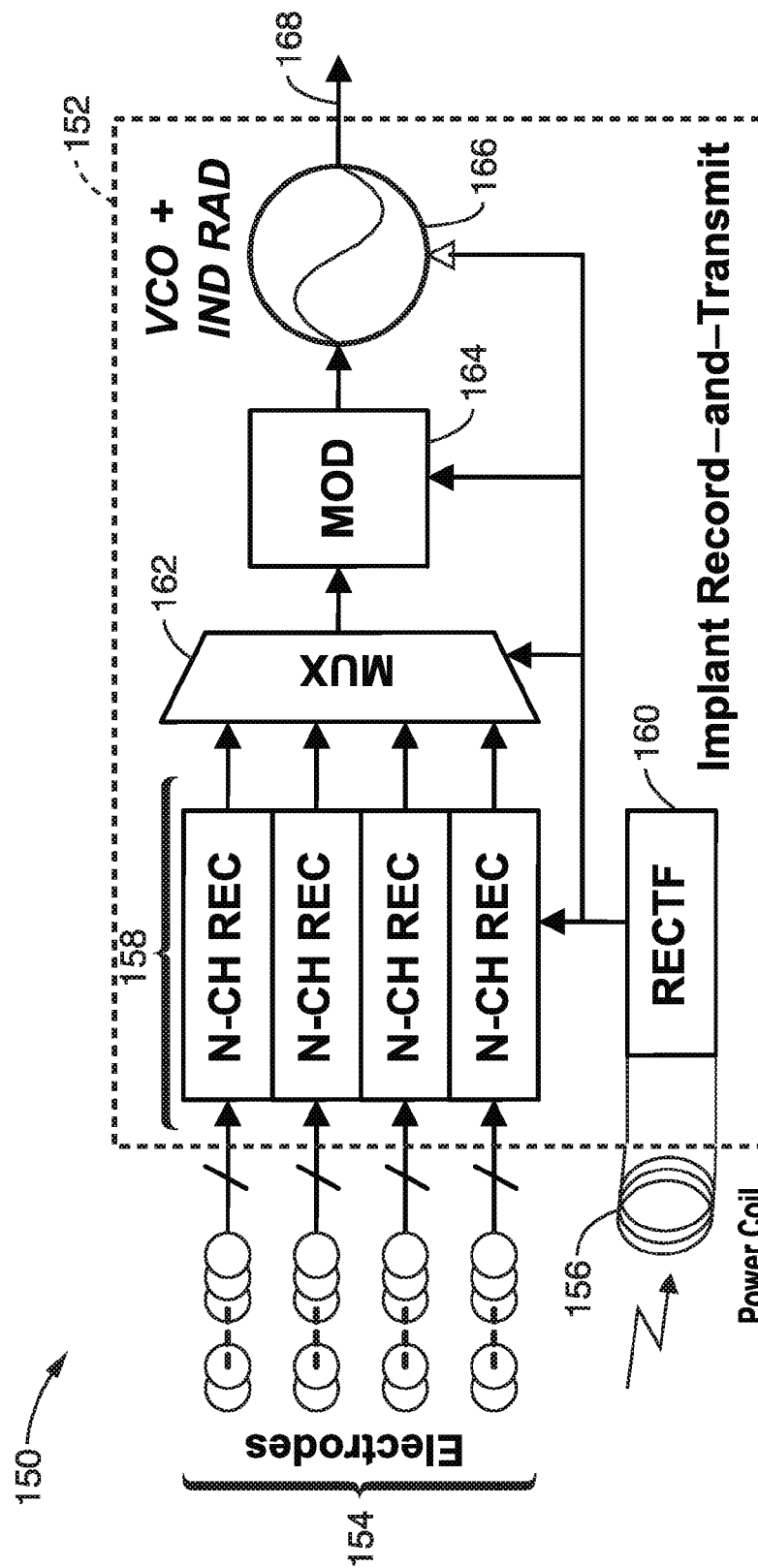
FIG. 5A is a block diagram of an implantable record-and-transmit module, utilizing an inductor within the VCO circuit as the radiator element according to at least one embodiment of the present disclosure.
Figure 5B:
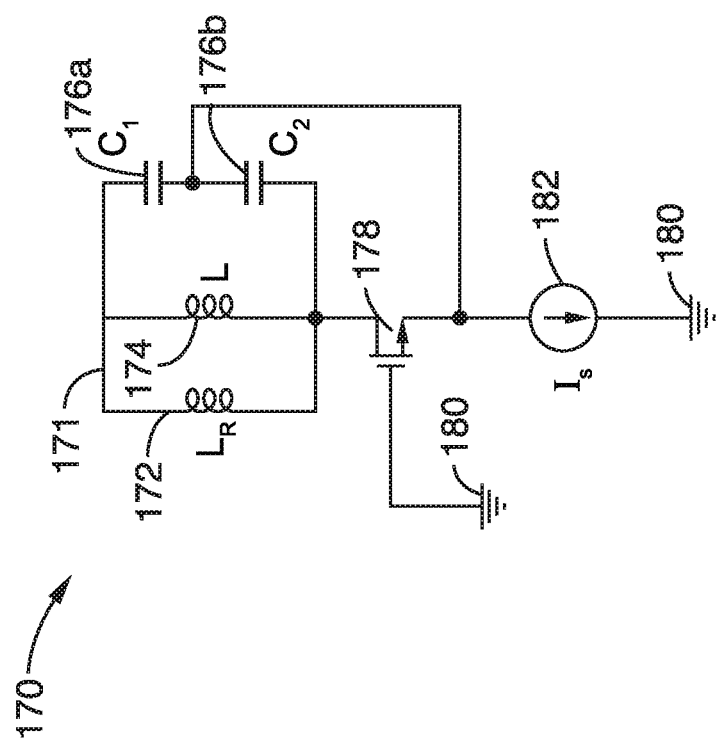
FIG. 5B is a schematic of a VCO circuit for use in FIG. 5A, which utilizes an inductor as the radiator element according to at least one embodiment of the present disclosure.

FIG. 5A and FIG. 5B illustrate an example embodiment 150, of an alternative to the implant record-and-transmit circuitry of FIG. 2. In this alternative, at least one component in the VCO, in this example an inductor, is utilized as the transmit radiator, thus merging the functionality of the radiator and the VCO. In FIG. 5A inputs are seen received at the implant record-and-transmit module (circuitry) 152 from multiple electrodes 154, while power is received through an inductive power coil 156. Multiple multi-channel neural recorders (REC) 158 record the neural information and output it to a multiplexer (MUX) (or serializer) 162, which aggregates these digitized outputs of the multiple recorders into a single bit-stream that drives modulator (MOD) 164, whose voltage signal output drives the voltage input of the voltage controlled oscillator (VCO) and combination radiator 166. It will be noted that a baseband signal input on the voltage input of a VCO operating at a carrier frequency significantly higher than baseband, results in the encoding of the baseband signal into a radio frequency output at the carrier frequency. It should be noted that although the inductor in the VCO is configured to radiate the signal, the schematic nonetheless depicts an output 168 by way of example.

FIG. 5B illustrates an example embodiment 170 of a combination VCO and radiator. Voltage control 171 drives a tank circuit comprising inductive radiator ($L_R$) 172 in parallel with inductor (L) 174, and a series pair of capacitors ($C_1$ and $C_2$) 176a, 176b, center coupled to provide feedback about the driving insulated gate field effect transistor (e.g., MOSFET) 178, whose gate is shown tied to ground 180 and whose source is coupled to a constant current source ($I_s$) 182 coupled to ground 180. The BMI apparatus of the present disclosure is not limited to this particular form of VCO as one of ordinary skill in the art will appreciate that scores of VCO circuits exist which could be utilized in the present disclosure without limitation.

Figure 6A:
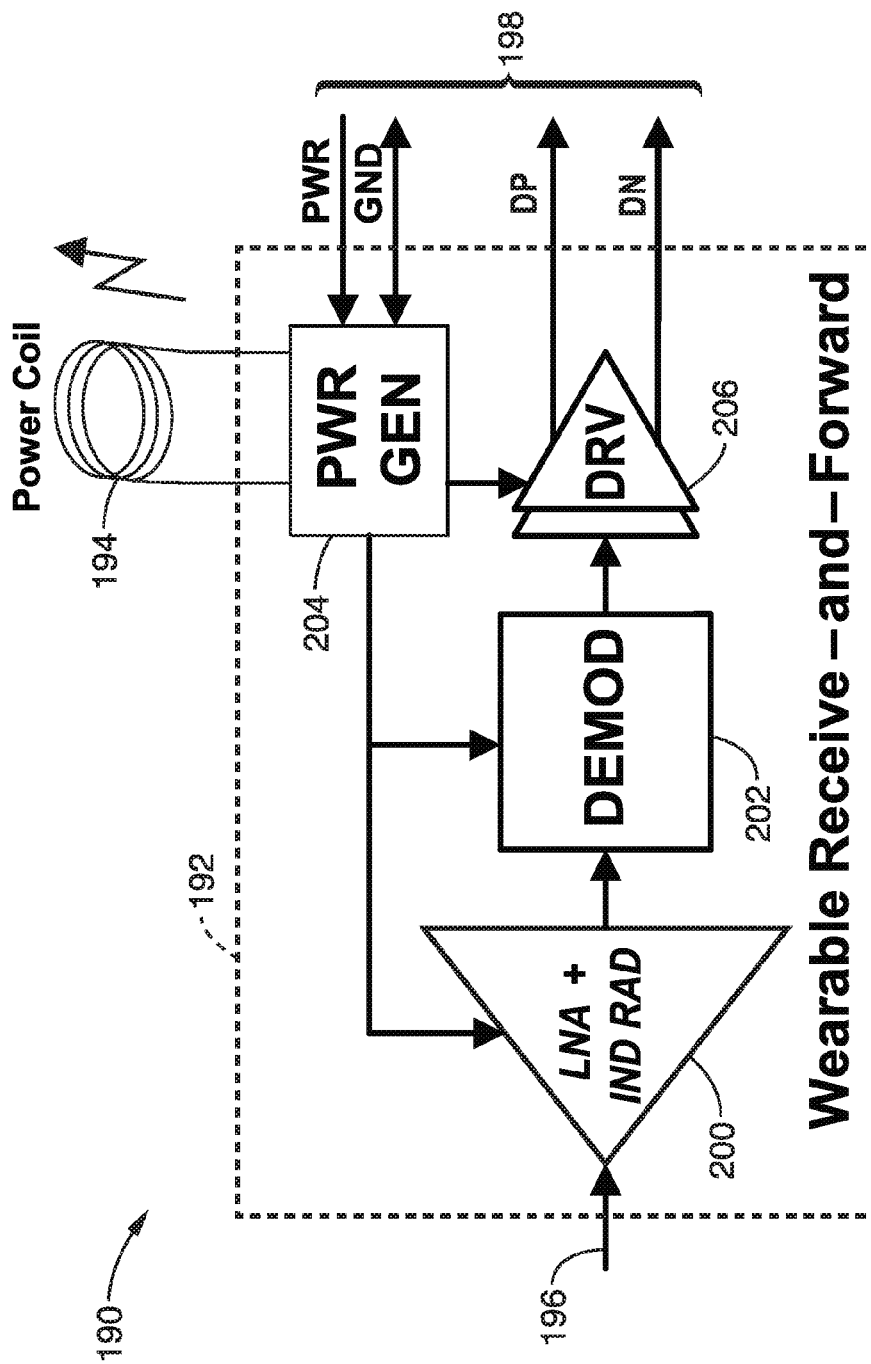
FIG. 6A is a block diagram of an wearable receive-and-forward module, utilizing an inductor within an amplifier circuit as the receiving radiator element according to at least one embodiment of the present disclosure.

FIG. 6A and FIG. 6B illustrate an example embodiment 190, of an alternative to the receive-and-forward circuitry of FIG. 3. In this alternative, the radiator of receive-and-forward circuitry 192 is combined with the LNA, that is to say that one or more components (e.g., inductor(s)) in the LNA receives the signal 196 from an implanted record-and-transmit circuit. This pair of implant and wearable modules can establish an inductive-coupling communication link for large data transfers. In FIG. 6A the alternative receive-and-forward circuitry 192 is seen with power coil 194, is configured for receiving external wireless signal 196, and has wired signals 198 comprising received power (PWR) and ground (GND), and differential outputs DN and DP. The radio frequency signal 196 is received by LNA 200 with inductive receiving radiator which outputs to a demodulator 202, which outputs to a drive circuit 206. Power to the inductive coil 194 and to the internal circuits is through a power generator (PWR GEN) 204. It will be appreciated that the drive circuit may be implemented to include clock recovery as was already seen in FIG. 3.

In FIG. 6B is illustrated an example embodiment 210 of the combination LNA with inductive radiator. Power (VDD) 212 is seen applied to a load, comprising inductor ($L_D$) 214 in parallel with a capacitor ($C_L$) 216 coupled to an insulated gate FET (e.g., MOSFET) biasing transistor 218 having a bias voltage ($V_b$) applied at its gate. Source from this first transistor is coupled to the drain of a second transistor 220, with its gate driven by signal 215 through a parallel pair of inductors ($L_g$) 214 in parallel the inductive radiator ($L_R$) 212. Source output on transistor 220 is through a source inductive load ($L_s$) 222 to ground 224.

Figure 7:
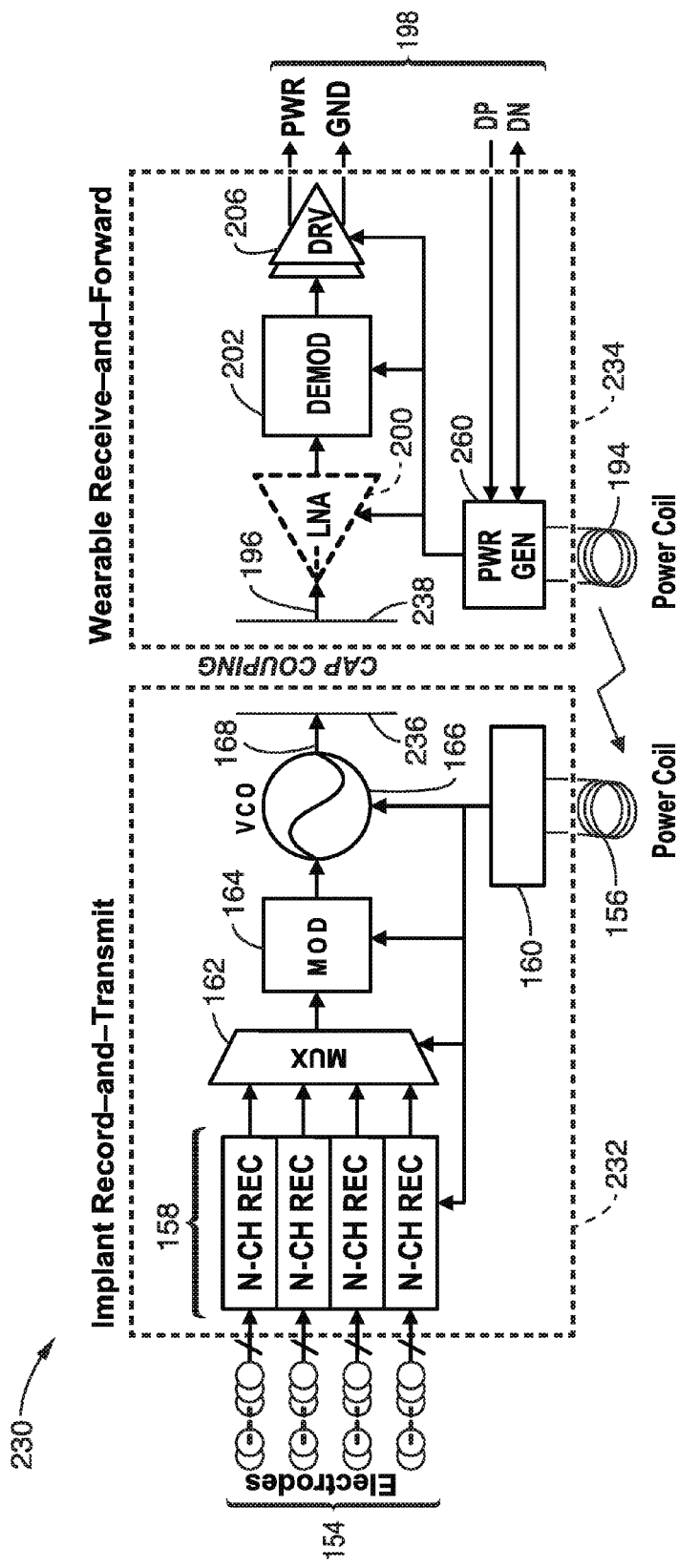
FIG. 7 is a block diagram of capacitor coupling between radiators in an implantable record-and-transmit module and a wearable receive-and-forward module according to at least one embodiment of the present disclosure.

FIG. 7 illustrates an example embodiment 230 of power and signal coupling between the implanted record-and-transmit unit 232 and wearable receive-and-forward unit 234. In this example, separate conductive plates 236, 238 are utilized as the radiators of the implant and wearable modules to establish a capacitive-coupling communication link, which can be used for large data transfers. It will be seen that the remainder of the circuit is as already described in regard to FIG. 5A and FIG. 6A, however the radiator in this case is not integrated within the VCO and LNA, as in those two previous examples. The power coupling is readily apparent in the figure between output power coil 156 and input power coil 194.

Figure 8:
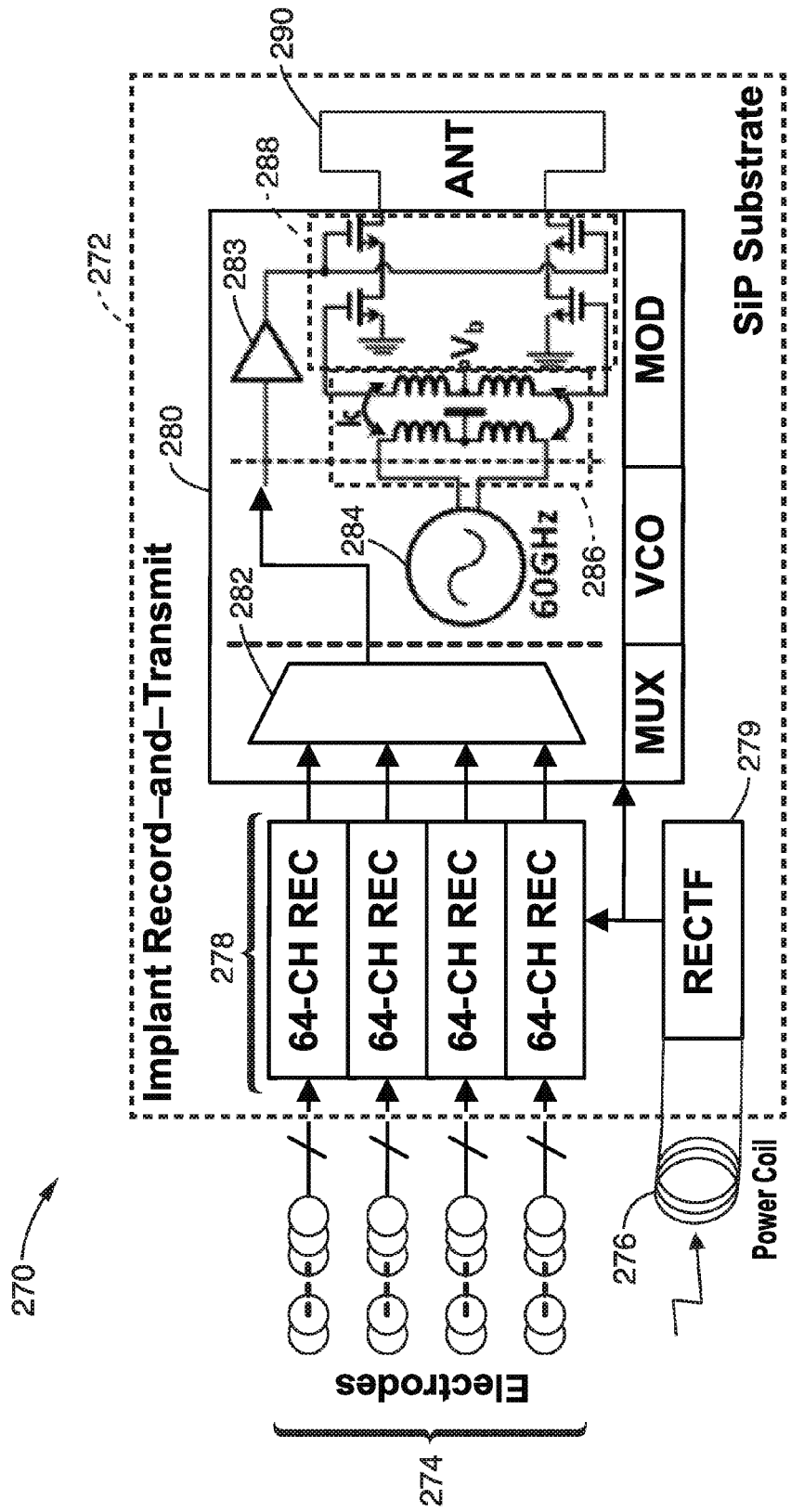
FIG. 8 is a block diagram of an implantable record-and-transmit module, showing an SiP implementation example, according to at least one embodiment of the present disclosure.
Figure 9:
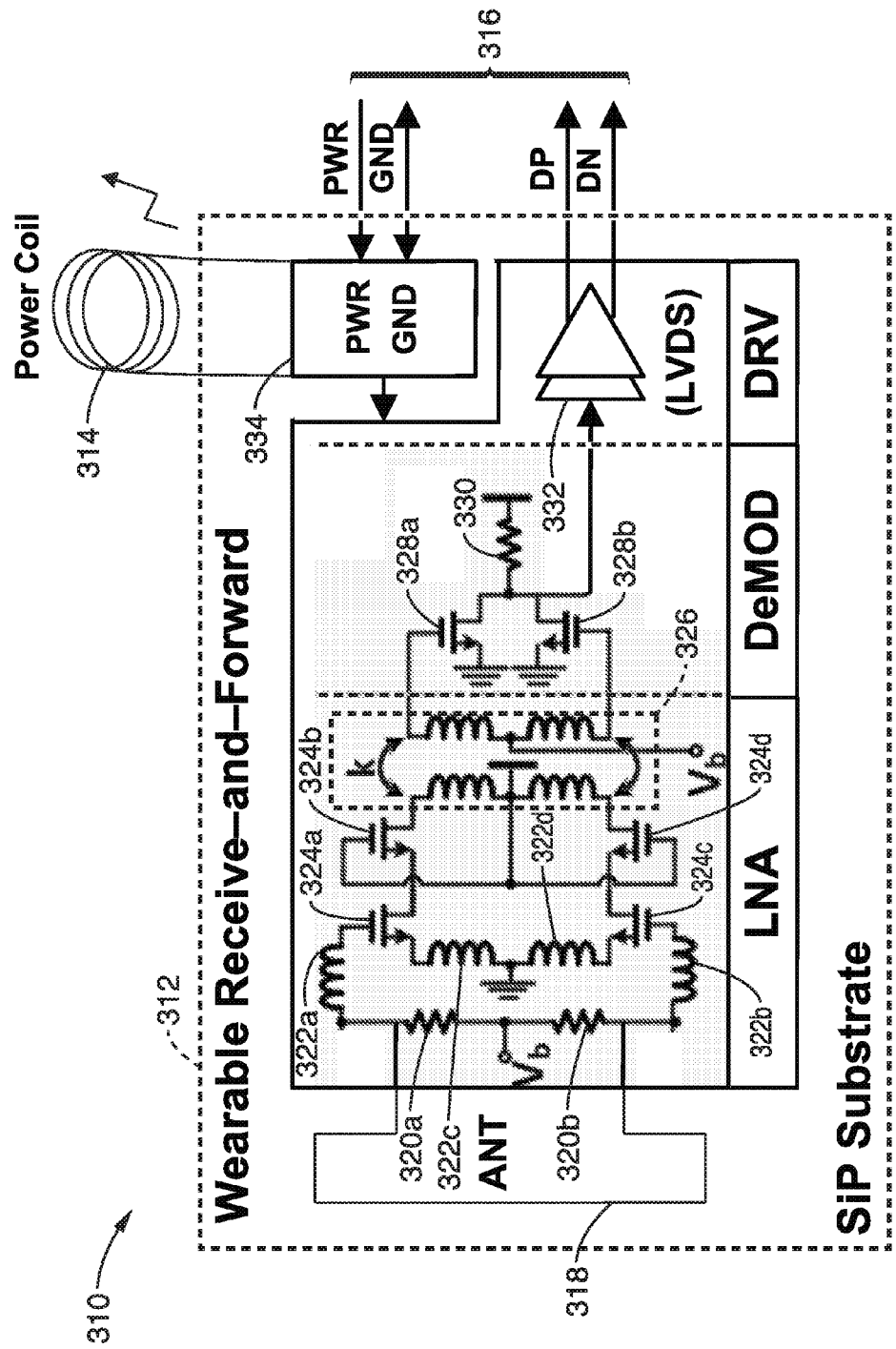
FIG. 9 is a block diagram of an wearable receive-and-forward module, showing an SiP implementation example, according to at least one embodiment of the present disclosure.

FIG. 8 and FIG. 9 illustrate additional embodiments of implanted record-and-transmit module 270 in FIG. 8 and wearable receive-and-forward module 310 in FIG. 9. By way of further example, these embodiments are shown being implemented utilizing a system-in-a-package (SiP) technology to fabricate these modules. It will be appreciated that SiP technology utilizes multiple chips assembled on substrates, with the antennas being preferably fabricated on the substrates themselves. In these figures the radiator/antenna is depicted as a dipole antenna, fabricated on the same substrate. The circuit implementations of modulator, LNA, and demodulator are shown in FIG. 8 and FIG. 9 as well.

In FIG. 8 the elements follow that of FIG. 2, exemplified here with additional details in the embodiment 270 with an implant recording and transmitting module 272. Inputs are received from multiple electrodes 274, with power received through inductive power coil 276. Within the module are seen multiple 64 channel neural recorders (REC) 278, each of which connects to multiple electrodes within the plurality of electrodes 274. Digitized recording outputs from the multiple recorders 278 are received in circuit block 280 by a multiplexer (MUX) (or serializer) 282, whose single bit-stream output is buffered 283 and drives modulation switches 288, shown comprising four insulated gate FET type transistors (e.g., MOSFETs). A carrier frequency source 284 is seen as a VCO coupled through an inductive bridge 286, to the modulator, which in response to the encoded data from MUX 282 changes output amplitude to dipole antenna 290, thus performing AM, or more precisely On-Off Keying (OOK) modulation of the carrier frequency for transmission. It will be recognized that On-Off Keying (OOK) is a form of AM modulation, in which the amplitudes comprise either the on or the off state.

Although AM/OOK modulation may be arguably the simplest to implement, it will be appreciated that the present disclosure is not limited to the use of AM/OOK, but is configured to utilize any desired data modulation types, such as selected from the group of modulation types comprising AM, FM, PSK, ASK, APSK, OOK, QPSK, PPM, QAM, SSB, SM, CSS, DSS, and so forth, which are known to those of ordinary skill in the art.

Power for the implanted circuitry is received from coil 276 into a rectifier module 279 that rectifies loop power and provides the necessary voltage levels for operating the circuitry in this implanted circuit.

In FIG. 9 the elements generally follow that of FIG. 3, exemplified here with additional details in the embodiment 310 with a wearable receive-and-forward module 312, shown with a power coil 314 and input/output signals 316. A modulated radio-frequency is received from the implant module in receive-and-forward module 312 on dipole antenna 318 coupled to a low noise amplifier (LNA) comprising resistors 320a, 320b, inductors 322a through 322d, and transistors 324a through 324d. Output from the amplifier is coupled to a modulator section through an inductive bridge 326 (output half being center-tap biased at voltage $V_b$) with demodulator having transistors 328a, 328b and resistor 330, which outputs to a low voltage differential drive circuit (LVDS) 332 for outputting differential signals DP and DN.

An inductive power generator circuit 334 is seen which receives power (e.g., PWR and GND) which is converted to proper voltages as necessary to supply its own circuitry, and to drive power coil 314 for inductive power coupling to the implant record-and-transmit circuit seen in FIG. 8. It should be reiterated, that the circuitry of the VCO, MOD, LNA, DeMOD, DRV, are shown here by way of example, and not by way of limitation, one of ordinary skill in the art will recognize that other circuits and variations may be employed without departing from the presented technology.

Figure 10:
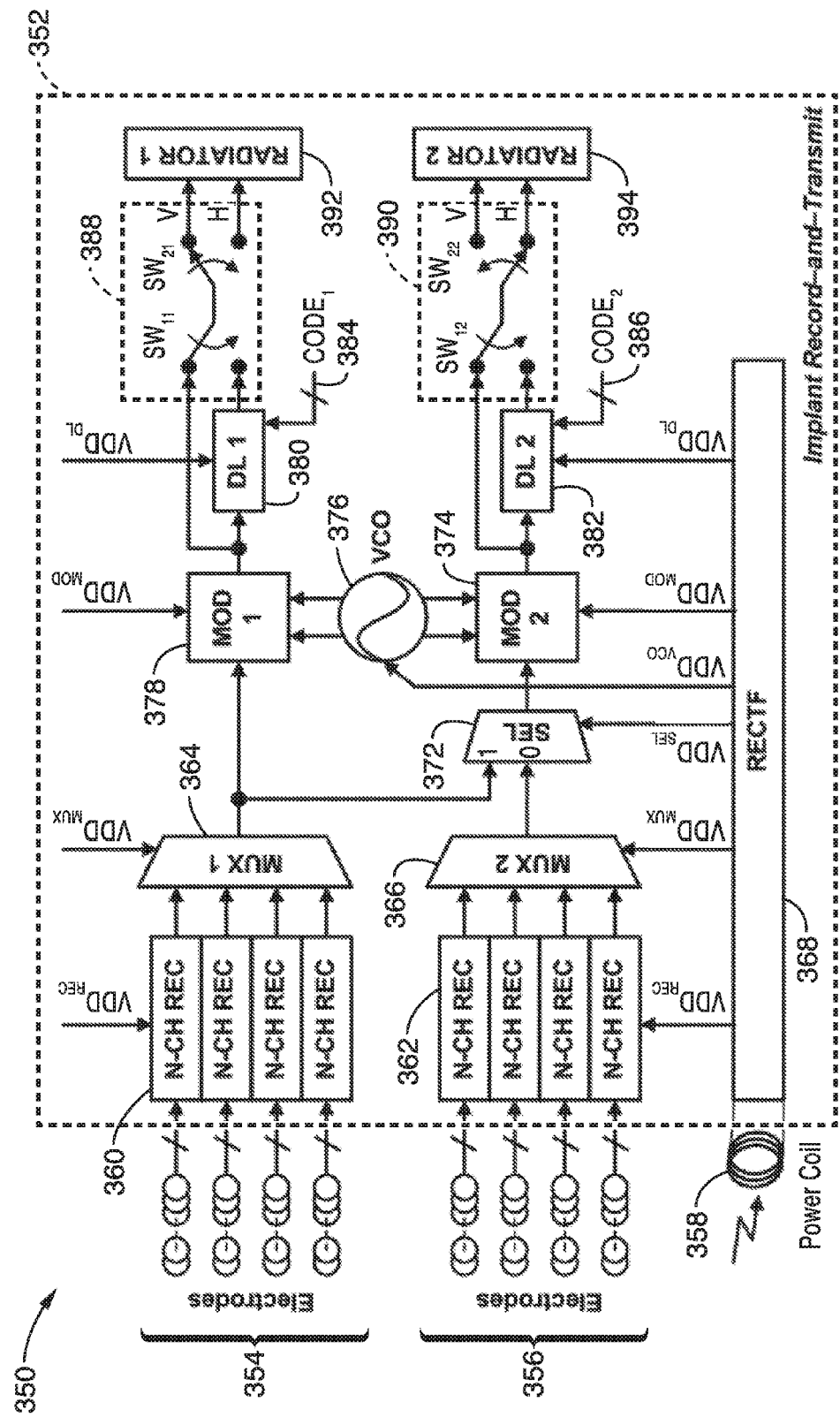
FIG. 10 is a block diagram of an extended data implantable record-and-transmit module according to at least one embodiment of the present disclosure.

FIG. 10 illustrates an example embodiment 350 of an extended version of the implanted record-and-forward functions seen in FIG. 2. This extended implant recording-and-transmitting module 352 supports double (2×) data rate transmission, and provides transmission beam alignment by setting up the switches: SW11, SW21, SW12, and SW22. In at least one embodiment of the present disclosure, transmission beam alignment is utilized so transmission and reception is performed simultaneously over multiple pairs of transmit/receive radiators in which the radiators in each of these pairs share the same orientation. In the example shown, transmission may be performed simultaneously through a vertical and horizontal radiator, and are also simultaneously received over a vertical and horizontal radiator. Utilizing this configuration allows doubling the data rate, without the concomitant need of two different carrier frequencies (channels).

It should be appreciated in these examples that the delay lines are utilized with the same polarizations for beam alignment, not for increasing the data rate; as only one modulator and one demodulator are involved. However, utilizing different polarizations without the delay lines provides for increasing the data rate, with multiple modulators and multiple demodulators are involved, but no beam alignment since no delay line involved.

It should also be appreciated that spatial separation of radiators may be utilized in certain embodiments as an alternative to utilizing different radiator orientations. The wireless radio frequency communications from the implanted record-and-transmit module to the wearable receive-and-forward module are broadcast over a short distance, thus, multiple radiators of even the same orientation could be utilized if they are sufficiently separated as long as they are still properly aligned with their respective receiving radiators. One significant drawback to this approach is the need to spatially distribute portions, to include at least the radiator elements, within both the implanted record-and-transmit module and the wearable receive-and-forward module. However, the technique can be utilized for providing any desired number of simultaneous short range wired communication links between the implanted and wearable devices.

Referring to FIG. 10, inputs are received from two sets of multiple electrodes 354, 356, into two sets of channel neural recorders (REC) 360, 362, whose outputs are received by respective multiplexers (MUXs) (or serializers) 364, 366, whose outputs can be selected for inclusion in the second bit stream by a selector 372. Modulators 374, 378, receive a carrier from VCO 376, and modulated radio frequency output of each respectively drive a programmable phase delay/time delay line (DL1, DL2) 380, 382, configured to receive a code 384, 386 for selecting the amount of delay. It should be appreciated that delay lines can be implemented in a wide range of types, including use of physical delays, propagation delays, a variety of sequential logic circuitry (shift-registers, etc.). and other circuit types and combinations thereof. As these are well known to one of ordinary skill in the art, their implementation is not discussed herein. Switching matrices 388, 390 provide for control of both alignment to radiators 392, 394, and for selecting whether to output modulated data in either real time (skipping the delay line), or after the programmed delay (passing through the delay line). The operation of these modes will be explained in greater detail in the example of FIG. 12 through FIG. 15.

The circuitry shown is powered from a rectification and power unit 368 which extracts power from the signal received on power coil 358. Rectification and power unit 368 supplies operating power to the internal circuitry in this figure, such as including $VDD_{REC}$, $VDD_{MUX}$, $VDD_{SEL}$, $VDD_{VCO}$, $VDD_{MOD}$ and $VDD_{DL}$.

Figure 11:
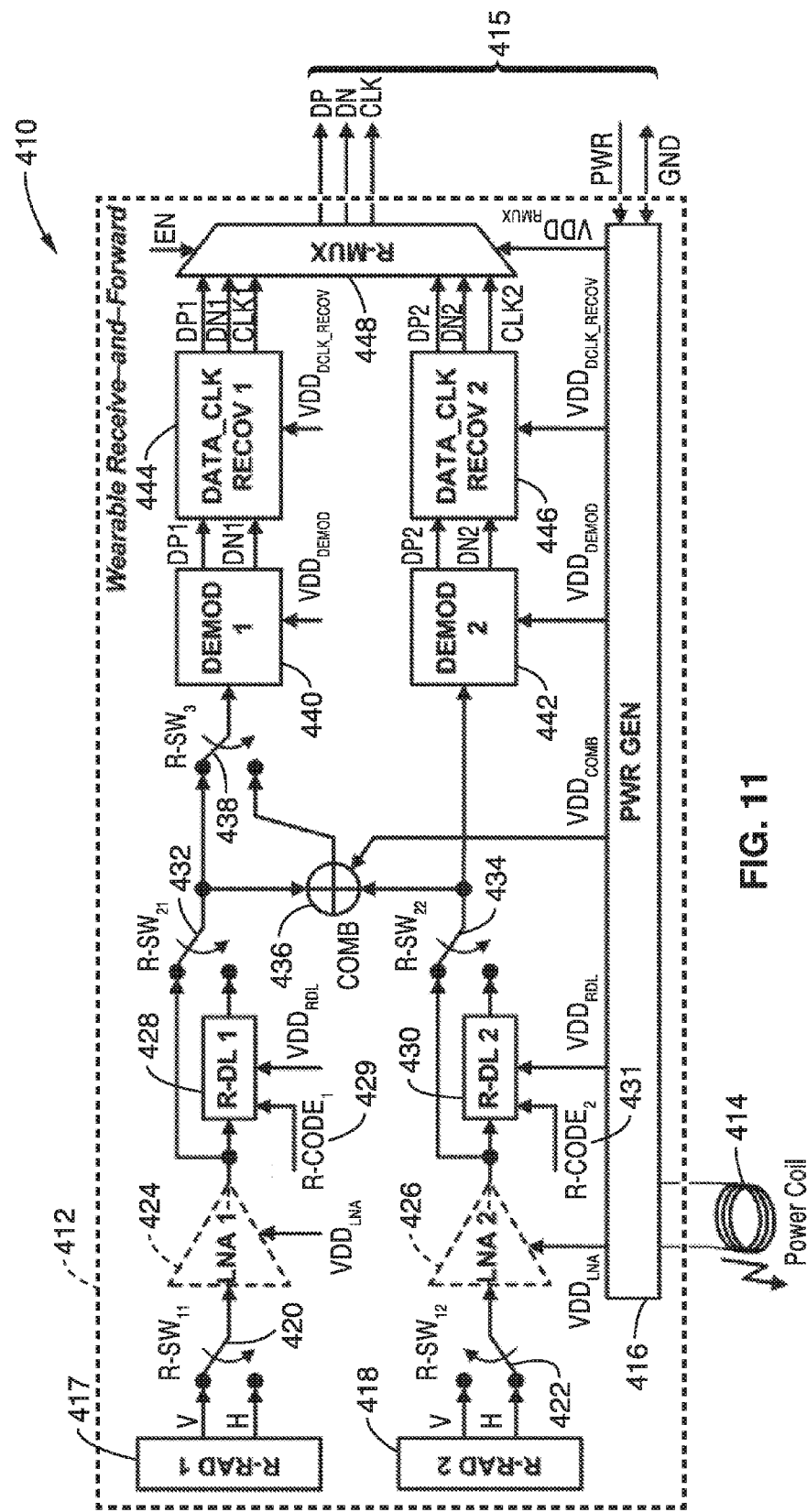
FIG. 11 is a block diagram of an extended data wearable receive-and-forward module according to at least one embodiment of the present disclosure.

FIG. 11 illustrates an example embodiment 410 of wearable receive-and-forwarding with corresponding wearable receive-and-forwarding module 412, which is configured for use with the implanted record-and-transmit circuitry shown in FIG. 10, supporting 2× data rate reception, and reception beam alignment utilizing switches: R-SW$_{11}$, R-SW$_{12}$, R-SW$_{21}$, R-SW$_{22}$, and R-SW$_{3}$. Module 412 is seen with power coupling coil 414, and wired signal I/O 415.

Power is generated from a power generator (PWR GEN) 416 on the wearable receiving and forwarding module which uses the power supplied through a wired interface (e.g., seen here as PWR and GND) to power its own circuitry, and to deliver power through attached power coil 414. Power from this coil is inductively coupled to a power coil and rectification circuit in the implant recording and transmitting module to supply power to this implanted device.

Radio frequencies are received by radiators 417 and 418, coupled to a switching network comprising R-SW$_{11}$ 420, R-SW$_{12}$ 422, R-SW$_{21}$ 432, R-SW$_{22}$ 434, and R-SW$_{3}$ 438. Switches R-SW$_{11}$ 420, R-SW$_{12}$ 422, perform selecting between vertical and horizontal orientations (polarizations). The received signals are then amplified by optional LNA circuits 424, 426, and received at dual receiver delay lines (phase-shift/time-delay) circuits (R-DL 1, R-DL 2) 428, 430 whose delay is programmed in response to respective R-code inputs 429, 431. It will be seen that switches R-SW$_{21}$, R-SW$_{22}$, allow selecting either between the delayed or non-delayed version of the data. The demodulators can receive the data (delayed or real time), while one of the modulators can be switched using switch R-SW$_{3}$ to instead receive the combination (COMB) 436 of this first and second channel with different phase shift amounts. So first demodulator (DEMOD 1) 440 receives real-time output from LNA 1, or output from R-DL 1, or a combination of outputs from LNA 1 and LNA 2, and outputs differential signals DP1, DP2 to a first data and clock recovery circuit (DATA_CLK RECOV 1) 444. In a similar subset operation, the second demodulator (DEMOD 2) 442 receives real-time output from LNA 2, or output from R-DL 2, and outputs its differential signals DP2, DN2 to a second data and clock recovery circuit (DATA_CLK RECOV 2) 446. Outputs from the data recovery units, including the differential outputs and clock are sampled at a multiplexor (R-MUX) 448 which outputs signals DP, DN and CLK.

FIG. 12 through FIG. 15 illustrate examples of implant and wearable modules for 2× data rate boosting, as seen in FIG. 10 and FIG. 11, which are shown here to demonstrate the use of two different radiator polarizations: vertical (V) and horizontal (H), and modes of operation. By selection of the different polarizations for radiators 1 and 2, for example: V for radiator 1 and H for radiator 2, the overall data rate can be doubled, without the need for utilizing two different carrier frequencies. It will be noted that in this particular implementation example, only one mode exists at a time.

Figure 12:
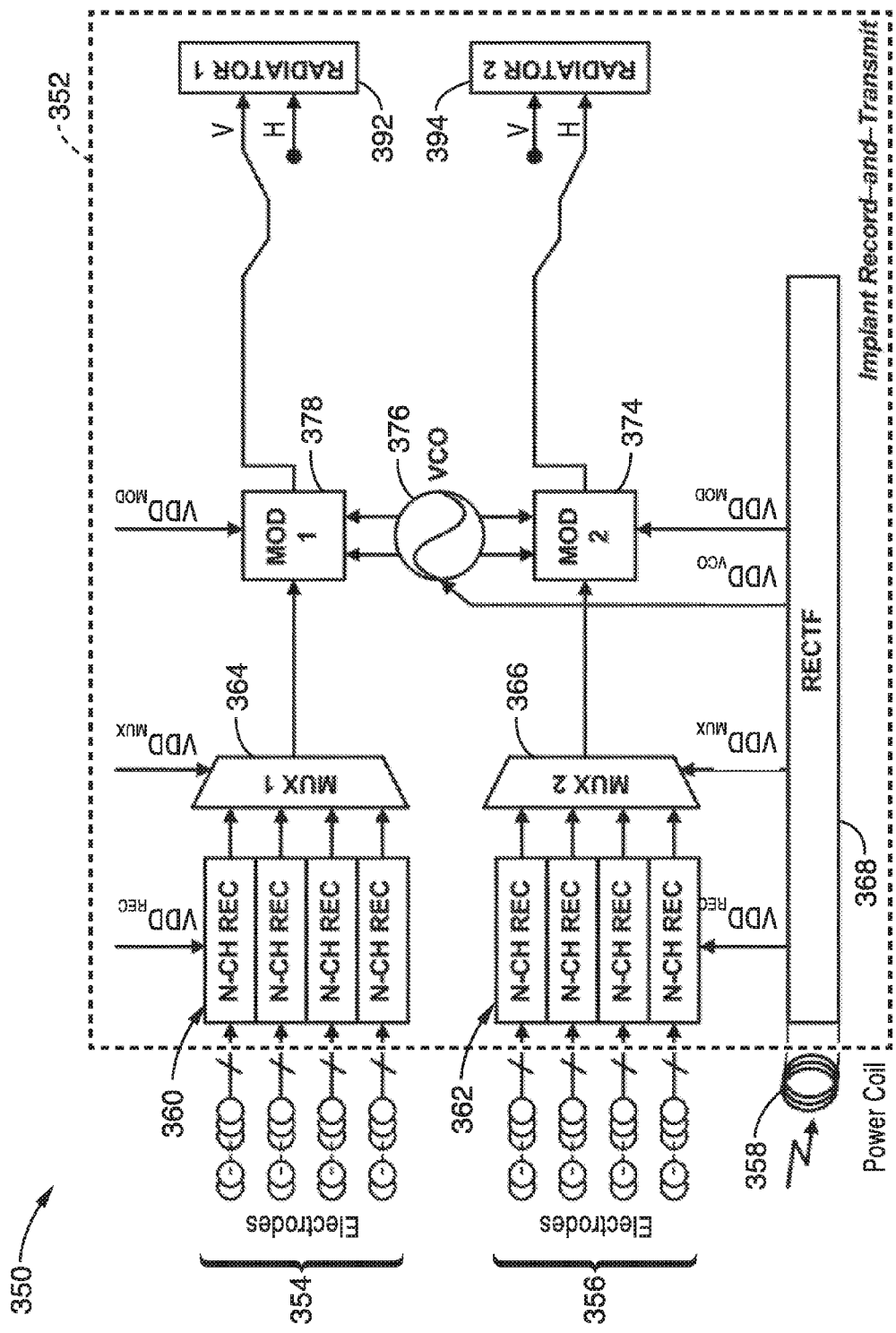
FIG. 12 is a block diagram of an extended data implantable record-and-transmit module, showing data path for a first operating mode, according to at least one embodiment of the present disclosure.
Figure 13:
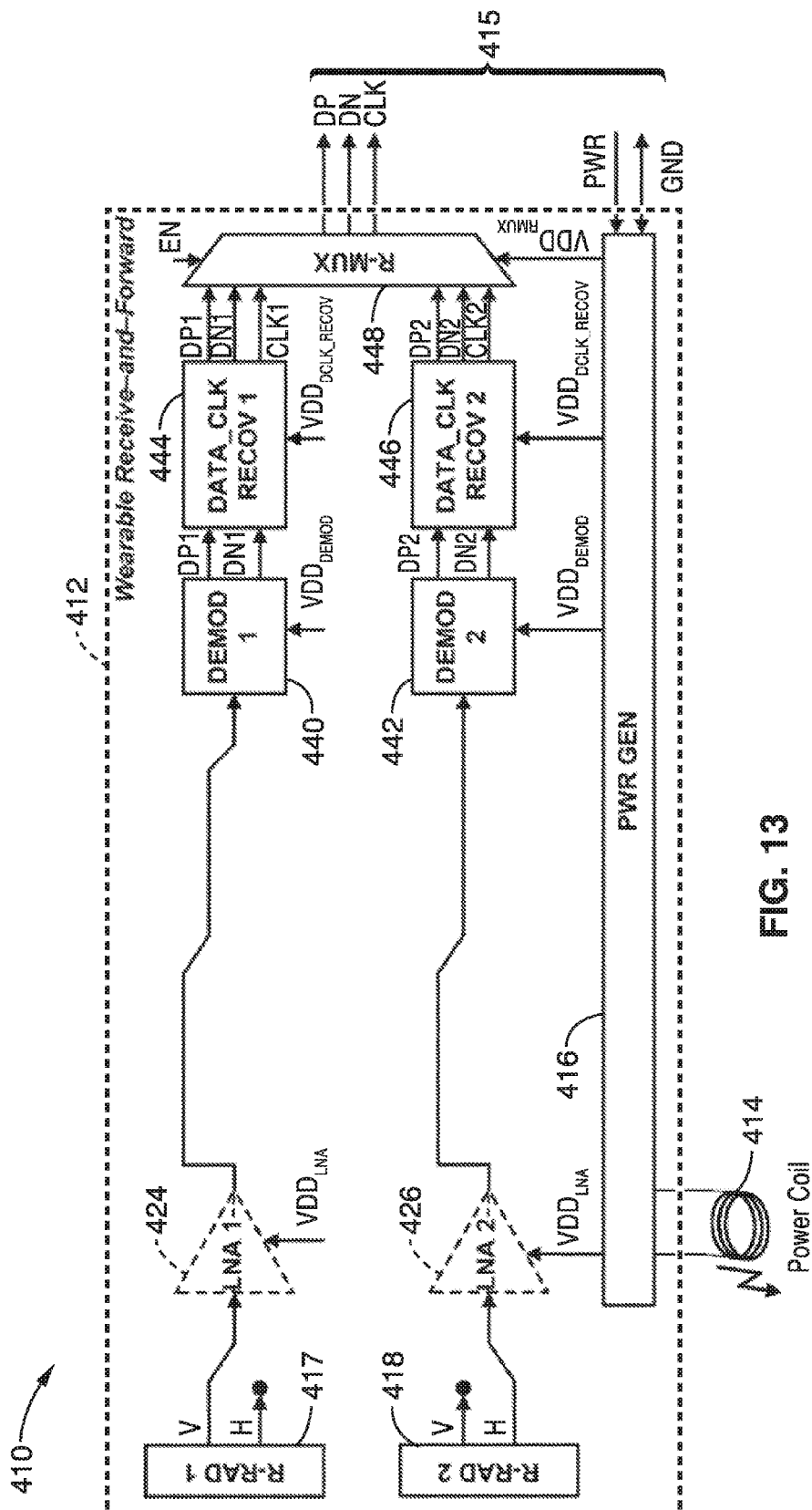
FIG. 13 is a block diagram of an extended data wearable receive-and-forward module, showing data path for a first operating mode, according to at least one embodiment of the present disclosure.
Figure 14:
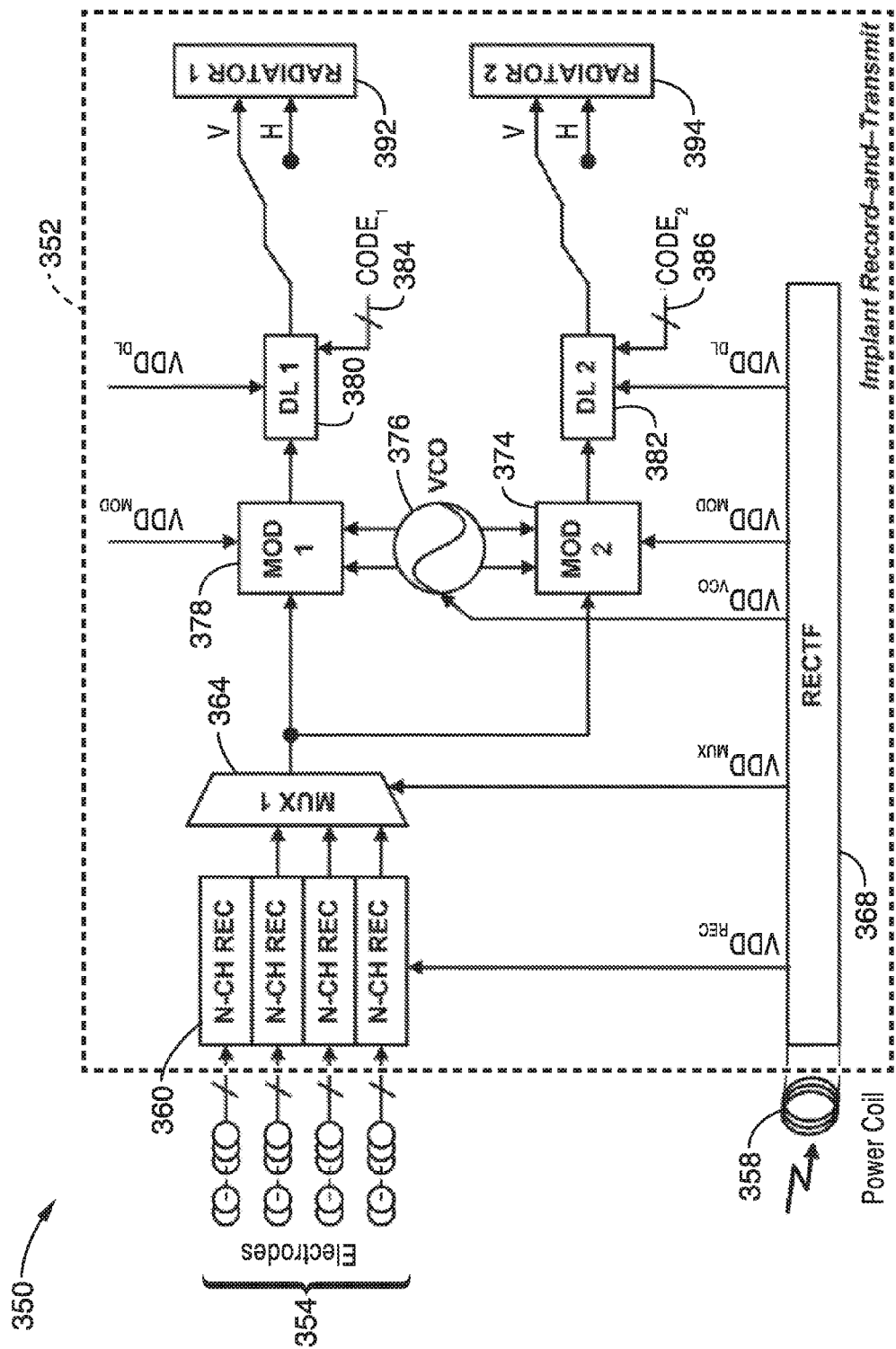
FIG. 14 is a block diagram of an extended data implantable record-and-transmit module, showing data path for a second operating mode, according to at least one embodiment of the present disclosure.
Figure 15:
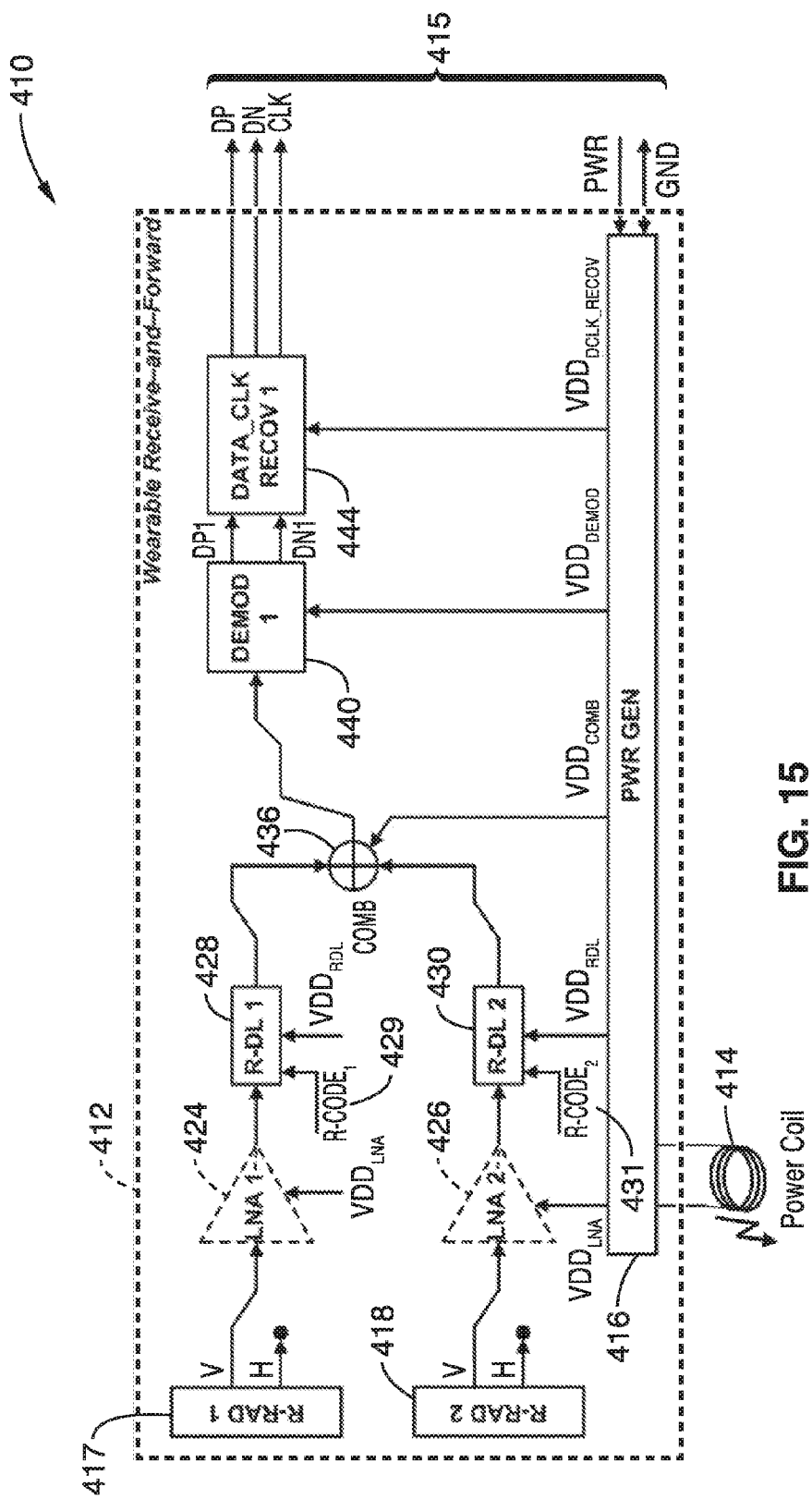
FIG. 15 is a block diagram of an extended data wearable receive-and-forward module, showing data path for a second operating mode, according to at least one embodiment of the present disclosure.

It will be noted that FIG. 12 and FIG. 14 are subsets of FIG. 10, while FIG. 13 and FIG. 15 are subsets of FIG. 11, as reflected in the reference numbering of each. To provide proper inter-module communication, it will be noted that the reciprocal radiators (R-RAD 1 and R-RAD 2) on the wearable module should have the same polarization configurations as on the implant module.

The combination of FIG. 12 and FIG. 13 illustrate signal connection/flow for the 1st mode (2× data rate boost). Setting the SW$_{11}$ and SW$_{21}$ to the up results in this mode (bypassing the transmission delay lines: DL1 and DL2). However, in this mode, (SW$_{12}$, SW$_{22}$) should be either (V, H) or (H, V), respectively.

In particular, FIG. 12 shows implant record-and-transmit module 352 with first radiator (RADIATOR 1) 392 selected for vertical (V) operation (polarization), while the second radiator (RADIATOR 2) 394 is selected for horizontal (H) operation.

In FIG. 13, the wearable receive-and-forward module 412 is also set in a position for receiving through radiator (R-RAD 1) 417 in a vertical direction, and through radiator (R-RAD 2) 418 in a horizontal direction.

The alternate modes are seen in FIG. 14 and FIG. 15, which do not operate in the 2× data rate boost modes. In FIG. 14 it is seen that delay lines (DL 1 and DL 2) 380, 382 are utilized to separate the output streams heading to the radiators (RADIATOR 1 and RADIATOR 2) 392, 394. Similarly, in FIG. 15 input from the radiators is passed through receiver delay lines (R-DL 1 and R-DL 2) 428, 430, and then combined in a combiner circuit 436 to generate a single bit stream output that is demodulated through DEMOD 440 and DATA_CLK RECOV 444 for output.

FIG. 16 depicts bit-error-rate (BER) performance degradation when the implant module (TX) and wearable module (RX) are not aligned properly. FIGS. 14 and 15 depicted the implant and wearable modules that can steer the transmission and reception beams, by changing programmed phase delays respectively, to mitigate this degradation. In this mode, the polarization configurations on all the radiators should be the same.

It will further be appreciated that "programming" as used herein refers to one or more instructions that can be executed by a processor to perform a function as described herein. The programming can be embodied in software, in firmware, or in a combination of software and firmware. The programming can be stored local to the device in non-transitory media, or can be stored remotely such as on a server, or all or a portion of the programming can be stored locally and remotely. Programming stored remotely can be downloaded (pushed) to the device by user initiation, or automatically based on one or more factors. It will further be appreciated that as used herein, that the terms processor, central processing unit (CPU), and computer are used synonymously to denote a device capable of executing the programming and communication with input/output interfaces and/or peripheral devices.

From the description herein, it will be appreciated that that the present disclosure encompasses multiple embodiments which include, but are not limited to, the following:

1. A wireless wearable brain machine interface apparatus, comprising: (a) an implanted recording and transmitting module, configured for receiving neural data from a plurality of implanted electrodes on a cranial region of a patient and wirelessly transmitting this neural data; (b) a wearable receiving and forwarding module configured for wirelessly receiving said neural data from said implanted recording and transmitting module; and (c) wherein said wearable receiving and forwarding module is configured for transmitting said neural data to a mobile post processing module.

2. The apparatus of any preceding embodiment, further comprising a mobile post processing module electrically connected to said wearable receiving and forwarding module and configured with a wireless communications interface for communicating said neural data to an external processor enabled device configured for processing and display of said neural data.

3. The apparatus of any preceding embodiment, further comprising a communications adapter integrated within, or coupled to, said wearable receiving and forwarding module which is configured for converting neural data received by said wearable receiving and forwarding module into another format prior to transmitting said neural data to a mobile post processing module.

4. The apparatus of any preceding embodiment, wherein the implant recording and transmitting module comprises: a plurality of multiple-channel neural recorders, each of which is configured for connection to a plurality of implanted electrodes from which neural data is received and recorded by said multiple-channel neural recorders which generate digitized recording outputs; at least one multiplexer or serializer configured for aggregating digitized outputs from said plurality of multiple-channel neural recorders to reduce the number of bit-streams; and at least one modulator configured for encoding said neural data into a radio frequency transmission.

5. The apparatus of any preceding embodiment, wherein the wearable receiving and forwarding module comprises: a demodulator configured for demodulating a radio frequency transmission from said implant recording and transmitting module to extract said neural data; and an output driver configured for outputting said neural data in a digital format over a wired interface for receipt by the mobile post processing module.

6. The apparatus of any preceding embodiment, further comprising: a power generator on said wearable receiving and forwarding module which uses power supplied through a wired interface to power its own circuitry, and to deliver power through an attached power coil; and a power coil and rectification circuit in said implant recording and transmitting module configured for inductively receiving power supplied between the power coil on said wearable receiving and forwarding module to said power coil in said implant recording and transmitting module, this power being rectified and utilized for powering the circuitry in said implant recording and transmitting module.

7. The apparatus of any preceding embodiment, wherein said wearable receiving and forwarding module is configured for retention within a wearable head covering, hat, headset, or set of glasses.

8. The apparatus of any preceding embodiment, wherein said implant recording and transmitting module communicates with said wearable receiving and forwarding module through a short-distance wireless link of approximately 1 cm in length.

9. The apparatus of any preceding embodiment, further comprising multiple transmission radiators on said implant recording and transmitting module, through which neural data is wirelessly transmitted at a rate higher than using a single radiator, to multiple reception radiators in said receiving and forwarding module.

10. The apparatus of any preceding embodiment, wherein each of said multiple transmission radiators on said implant recording and transmitting module are configured with different amount of time delay to provide beam alignment between these radiators and radiators with matching alignments in the wearable record and forward module to which neural data is wirelessly transmitted.

11. The apparatus of any preceding embodiment, wherein data rate of said neural data being collected and transmitted by said implant record and transmit module is approximately 1 Gb/second, or higher.

12. A wireless wearable brain machine interface apparatus, comprising: (a) an implanted recording and transmitting module configured for electrical connection to a plurality of electrodes implanted on a cranial region of a patient, from which neural data is registered and wirelessly transmitted; (b) a wearable receiving and forwarding module configured for being wearably retained, and not implanted, near the cranium region of the patient proximal said implanted recording and transmitting module, said wearable receiving and forwarding module configured for receiving wireless transmissions of neural data from said proximal implanted recording and transmitting module; and (c) wherein said wearable receiving and forwarding module is configured for formatting said neural data and transmitting it to a mobile post processing module.

13. The apparatus as of any preceding embodiment, wherein said implanted recording and transmitting module, comprises: (i) multiple N-channel recorders configured for storing neural data from a plurality of electrodes coupled to each of said N-channel recorders; (ii) at least one multiplexor configured for multiplexing neural data signals from a number of said N-channel recorders into a single bit stream; and (iii) at least one modulator configured for converting each single bit stream from a multiplexor by modulating a carrier frequency with each said single bit stream into a wireless radio frequency signal for transmission through a radiating element.

14. The apparatus as of any preceding embodiment, wherein said wearable receiving and forwarding module comprises: (i) a radiator or antenna configured for receiving said radio frequency signal from said implanted recording and transmitting module; and (ii) a demodulator configured for extracting each said single bit stream of neural data from said wireless radio frequency signal.

15. The apparatus as of any preceding embodiment, further comprising a power generation circuit in said wearable receiving and forwarding module configured for powering an inductive power coil as an inductively coupled power source to the power coil of said implanted recording and transmitting module, which rectifies and distributes this as operating power to its circuitry.

16. The apparatus of any preceding embodiment, further comprising a mobile post processing module electrically connected to said wearable receiving and forwarding module through which neural data is received, and said mobile post processing module is also configured with a wireless communications interface for communicating said neural data to an external processor enabled device configured for processing and display of said neural data.

17. The apparatus of any preceding embodiment, further comprising a communications adapter integrated within, or coupled to, said wearable receiving and forwarding module which is configured for converting neural data received by said wearable receiving and forwarding module into another format prior to transmitting said neural data to a mobile post processing module.

18. The apparatus of any preceding embodiment, further comprising: a power generator on said wearable receiving and forwarding module which uses power supplied through a wired interface to power its own circuitry, and to deliver power through an attached power coil; and a power coil and rectification circuit in said implant recording and transmitting module configured for inductively receiving power supplied between the power coil on said wearable receiving and forwarding module to said power coil in said implant recording and transmitting module, this power being rectified and utilized for powering the circuitry in said implant recording and transmitting module.

19. The apparatus of any preceding embodiment, wherein said wearable receiving and forwarding module is configured for retention within a wearable head covering, hat, headset, or set of glasses.

20. The apparatus of any preceding embodiment, wherein said implant recording and transmitting module communicates with said wearable receiving and forwarding module through a short-distance wireless link of approximately 1 cm in length.

21. The apparatus of any preceding embodiment, further comprising multiple transmission radiators on said implant recording and transmitting module, through which neural data is wirelessly transmitted at a rate higher than using a single radiator, to multiple reception radiators in said receiving and forwarding module.

22. The apparatus of any preceding embodiment, wherein each of said multiple transmission radiators on said implant recording and transmitting module are configured with different amount of time delay to provide beam alignment between these radiators and radiators with matching alignments in the wearable record and forward module to which neural data is wirelessly transmitted.

23. The apparatus of any preceding embodiment, wherein data rate of said neural data being collected and transmitted by said implant record and transmit module is approximately 1 Gb/second, or higher.

24. A wireless wearable brain machine interface apparatus, comprising: (a) an implanted recording and transmitting module configured for connection to a plurality of electrodes implanted on a cranial region of a patient, said implanted recording and transmitting module including: (a)(i) multiple N-channel recorders configured for storing neural data from a plurality of electrodes coupled to each of said N-channel recorders; (a)(ii) at least one multiplexor configured for multiplexing neural data signals from a number of said N-channel recorders into a single bit stream; (a)(iii) at least one modulator configured for converting each single bit stream from a multiplexor by modulating a carrier frequency with each said single bit stream into a wireless radio frequency signal for transmission through a radiating element; (b) a wearable receiving and forwarding module configured for being wearably retained, and not implanted, near the patient's cranium proximal to said implanted recording and transmitting module, said wearable receiving and forwarding module including: (b)

(i) a radiator or antenna configured for receiving said radio frequency signal from said implanted recording and transmitting module; (b)(ii) a demodulator configured for extracting each said single bit stream of neural data from said wireless radio frequency signal; and (c) a mobile post processing module configured for receiving at least one of said single bit stream and performing post-processing of the neural data in response to programming executing on a computer processor within said mobile post processing module; wherein said mobile post processing module is configured for being worn by the patient while said neural data is being collected.

25. A wireless wearable brain machine interface apparatus, comprising: (a) an implanted recording and transmitting module configured for connection to a plurality of electrodes implanted on a patient's cranium, said implanted recording and transmitting module including: (a)(i) a power coil and rectification circuit configured for receiving power from an inductively coupled power source; (a) (ii) multiple N-channel recorders configured for storing neural data from a plurality of electrodes coupled to each of said N-channel recorders; (a)(iii) at least one multiplexor configured for multiplexing neural data signals from a number of said N-channel recorders into a single bit stream; (a)(iv) at least one modulator configured for converting each single bit stream from a multiplexor by modulating a carrier frequency with each said single bit stream into a wireless radio frequency signal for transmission through a radiating element; (b) a wearable receiving and forwarding module configured for being wearably retained, and not implanted, near the patient's cranium proximal to said implanted recording and transmitting module, said wearable receiving and forwarding module including: (b)(i) a power generation circuit configured for powering an inductive power coil as the inductively coupled power source to the power coil of said implanted recording and transmitting module; (b)(ii) a radiator or antenna configured for receiving said radio frequency signal from said implanted recording and transmitting module; (b)(iii) a demodulator configured for extracting each said single bit stream of neural data from said wireless radio frequency signal; and (c) a mobile post processing module configured for receiving at least one of said single bit stream and performing post-processing of the neural data in response to programming executing on a computer processor within said mobile post processing module; wherein said mobile post processing module is configured for being worn by the patient while said neural data is being collected.

26. A wireless wearable big data brain machine interface apparatus, comprising: an implant recording and transmitting module; and a wearable receiving and forwarding module; and said implant recording and transmitting module, and said wearable receiving and forwarding module, each including a wireless communications interface.

27. The apparatus of any preceding embodiment, wherein the implant recording and transmitting module comprises: a plurality of multi-channel neural recorders (REC), each of which connects to a plurality of electrodes, and generates digitized recording outputs; a multiplexer (MUX)/serializer, which aggregates the digitized outputs of the plurality of recorders into a single bit-stream; a modulator (MOD), which uses the single bit-stream output of the MUX to generate control signals (e.g. on/off) to control a VCO; a voltage control oscillator (VCO), which generates a carrier, preferably at a frequency of over 5 GHz, and of which the output can be turned on/off based on the MOD output; a radiator (RAD), which radiates the VCO output from the implant module to other medium; and a rectifier (RECTF), which receives the wireless power through an attached power coil, and converts the received power to various DC voltages supplying the aforementioned modules (RECs, MUX, MOD, and VCO) except the radiator.

28. The apparatus of any preceding embodiment, wherein the wearable receiving and forwarding module comprises: a radiator (RAD), which receives the signals radiated by the RAD of the implant module and delivers the received signals to a LNA or DEMOD; an optional low noise amplifier (LNA), which amplifies the received signals for the input of a DEMOD; a demodulator (DEMOD), which demodulates the received (or the received and amplified) signals into a single-ended bit-stream running at the symbol rate that is much slower than the carrier frequency (5+ GHz); a driver (DRV), which converts the single-ended DEMOD output into a differential one to accommodate potential signal integrity issues of wire data transfer/forwarding; and a power generator (PWR GEN), which uses the power supplied through the wire interface, delivers a portion of the supplied power to the implant module thorough the attached power coil, and generates the required DC voltages for LNA, DEMOD and DRV; wherein the DRV differential outputs—DP and DN, the supplied power—PWR, and the ground reference—GND constitute a four-wire interface. It will be noted that if DATA_CLK_RECOV is utilized, then a five-wire interface is provided. The number of wires and composition of the interface is determined by the specific circuitry utilized, which is subject to variation without departing from the teachings of the present disclosure.

29. The apparatus of any preceding embodiment, further comprising: a mobile post processing module; said mobile post processing module connected to said wearable receiving and forwarding module; said mobile post processing module including a wireless communications interface.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A wireless wearable brain machine interface apparatus, comprising:
   (a) an implant recording and transmitting module, configured for receiving neural data from a plurality of implant electrodes on a cranial region of a patient and wirelessly transmitting said neural data, said implant recording and transmitting module comprising:
      (i) a plurality of multiple-channel neural recorders, each of which is configured for connection to a plurality of implant electrodes from which neural data is received and recorded by said multiple-channel neural recorders which sample neural signals at a sampling rate and convert neural levels through analog-to-digital converters (ADCs) to generate multiple digitized recording outputs;
      (ii) at least one multiplexer or serializer configured for aggregating digitized outputs from said plurality of multiple-channel neural recorders to reduce the number of bit-streams; and
      (iii) at least one modulator configured for encoding said neural data into a digital radio frequency transmission;
   (b) a wearable receiving and forwarding module configured for wirelessly receiving said neural data from said implant recording and transmitting module;
   (c) a mobile post processing module configured for receiving transmissions from said wearable receiving and forwarding module which is configured for transmitting said neural data to said mobile post processing module; and
   (d) wherein said mobile post processing module is configured for performing feature extraction and compression on said neural data and wirelessly transmitting neural information to a remote computer-enabled electronic device configured for viewing, storing, and/or manipulating said neural information.

2. The apparatus as recited in claim 1, further comprising a mobile post processing module electrically connected to said wearable receiving and forwarding module and configured with a wireless communications interface for communicating said neural data to an external processor enabled device configured for processing and display of said neural data.

3. The apparatus as recited in claim 1, further comprising a communications adapter integrated within, or coupled to, said wearable receiving and forwarding module which is configured for converting neural data received by said wearable receiving and forwarding module into another format prior to transmitting said neural data to a mobile post processing module.

4. The apparatus as recited in claim 1, wherein the wearable receiving and forwarding module comprises:
   a demodulator configured for demodulating a radio frequency transmission from said implant recording and transmitting module to extract said neural data; and
   an output driver configured for outputting said neural data in a digital format over a wired interface for receipt by the mobile post processing module.

5. The apparatus as recited in claim 1, further comprising:
   a power generator on said wearable receiving and forwarding module which uses power supplied through a wired interface to power its own circuitry, and to deliver power through an attached power coil; and
   a power coil and rectification circuit in said implant recording and transmitting module configured for inductively receiving power supplied between the power coil on said wearable receiving and forwarding module to said power coil in said implant recording and transmitting module, this power being rectified and utilized for powering the circuitry in said implant recording and transmitting module.

6. The apparatus as recited in claim 1, wherein said wearable receiving and forwarding module is configured for retention within a wearable head covering, hat, headset, or set of glasses.

7. The apparatus as recited in claim 1, wherein said implant recording and transmitting module communicates with said wearable receiving and forwarding module through a short-distance wireless link of approximately 1 cm in length.

8. The apparatus as recited in claim 1, further comprising multiple transmission radiators on said implant recording and transmitting module, through which neural data is wirelessly transmitted at a rate higher than using a single radiator, to multiple reception radiators in said receiving and forwarding module.

9. The apparatus as recited in claim 8, wherein each of said multiple transmission radiators on said implant recording and transmitting module are configured with different amount of time delay to provide beam alignment between these radiators and radiators with matching alignments in the wearable record and forward module to which neural data is wirelessly transmitted.

10. The apparatus as recited in claim 1, wherein data rate of said neural data being collected and transmitted by said implant record and transmit module is approximately 1 Gb/second, or higher.

11. A wireless wearable brain machine interface apparatus, comprising:
   (a) an implant recording and transmitting module configured for electrical connection to a plurality of electrodes implant on a cranial region of a patient, from which neural data is registered and wirelessly transmitted, said implant recording and transmitting module, comprising:
      (i) multiple N-channel recorders configured for storing neural data from a plurality of electrodes coupled to each of said N-channel recorders, which sample neural signals at a sampling rate and convert neural levels though analog-to-digital converters (ADCs) to generate multiple digitized recording outputs;
      (ii) at least one multiplexor configured for multiplexing neural data signals from a number of said N-channel recorders into a single bit stream; and
      (iii) at least one modulator configured for converting each single bit stream from a multiplexor by modulating a carrier frequency with each said single bit stream into a wireless digital radio frequency signal for transmission through a radiating element;
   (b) a wearable receiving and forwarding module configured for being wearably retained, and not implant, near the cranium region of the patient proximal said implant recording and transmitting module, said wearable receiving and forwarding module configured for receiving wireless transmissions of neural data from said proximal implant recording and transmitting module;
   (c) a mobile post processing module configured for receiving transmissions from said wearable receiving and forwarding module which is configured for formatting said neural data and transmitting it to said mobile post processing module; and
   (d) wherein said mobile post processing module is configured for performing feature extraction and compression on said neural data and wirelessly transmitting neural information to a remote computer-enabled electronic device configured for viewing, storing, and/or manipulating said neural information.

12. The apparatus as recited in claim 11, wherein said wearable receiving and forwarding module comprises:
   (i) a radiator or antenna configured for receiving said radio frequency signal from said implant recording and transmitting module; and
   (ii) a demodulator configured for extracting each said single bit stream of neural data from said wireless radio frequency signal.

13. The apparatus as recited in claim 11, further comprising a power generation circuit in said wearable receiving and forwarding module configured for powering an inductive power coil as an inductively coupled power source to the power coil of said implant recording and transmitting module, which rectifies and distributes this as operating power to its circuitry.

14. The apparatus as recited in claim 11, further comprising a mobile post processing module electrically connected to said wearable receiving and forwarding module through which neural data is received, and said mobile post processing module is also configured with a wireless communications interface for communicating said neural data to an external processor enabled device configured for processing and display of said neural data.

15. The apparatus as recited in claim 11, further comprising a communications adapter integrated within, or coupled to, said wearable receiving and forwarding module which is configured for converting neural data received by said wearable receiving and forwarding module into another format prior to transmitting said neural data to a mobile post processing module.

16. The apparatus as recited in claim 11, further comprising:
   a power generator on said wearable receiving and forwarding module which uses power supplied through a wired interface to power its own circuitry, and to deliver power through an attached power coil; and a power coil and rectification circuit in said implant recording and transmitting module configured for inductively receiving power supplied between the power coil on said wearable receiving and forwarding module to said power coil in said implant recording and transmitting module, this power being rectified and utilized for powering the circuitry in said implant recording and transmitting module.

17. The apparatus as recited in claim 11, wherein said wearable receiving and forwarding module is configured for retention within a wearable head covering, hat, headset, or set of glasses.

18. The apparatus as recited in claim 11, wherein said implant recording and transmitting module communicates with said wearable receiving and forwarding module through a short-distance wireless link of approximately 1 cm in length.

19. The apparatus as recited in claim 11, further comprising multiple transmission radiators on said implant recording and transmitting module, through which neural data is wirelessly transmitted at a rate higher than using a single radiator, to multiple reception radiators in said receiving and forwarding module.

20. The apparatus as recited in claim 19, wherein each of said multiple transmission radiators on said implant recording and transmitting module are configured with different amount of time delay to provide beam alignment between these radiators and radiators with matching alignments in the wearable record and forward module to which neural data is wirelessly transmitted.

21. The apparatus as recited in claim 11, wherein data rate of said neural data being collected and transmitted by said implant record and transmit module is approximately 1 Gb/second, or higher.

22. A wireless wearable brain machine interface apparatus, comprising:
(a) an implant recording and transmitting module configured for connection to a plurality of electrodes implant on a cranial region of a patient, said implant recording and transmitting module comprising:
  (i) multiple N-channel recorders configured for storing neural data from a plurality of electrodes coupled to each of said N-channel recorders which sample neural signals and convert neural levels to generate multiple digitized recording outputs;
  (ii) at least one multiplexor configured for multiplexing neural data signals from a number of said N-channel recorders into a single bit stream; and
  (iii) at least one modulator configured for converting each single bit stream from a multiplexor by modulating a carrier frequency with each said single bit stream into a wireless radio frequency signal for transmission through a radiating element;
(b) a wearable receiving and forwarding module configured for being wearably retained, and not implant, near the patient's cranium proximal to said implant recording and transmitting module, said wearable receiving and forwarding module comprising:
  (i) a radiator or antenna configured for receiving said radio frequency signal from said implant recording and transmitting module; and
  (ii) a demodulator configured for extracting each said single bit stream of neural data from said wireless radio frequency signal;
(c) a mobile post processing module configured for receiving at least one of said single bit stream and performing post-processing of the neural data in response to programming executing on a computer processor within said mobile post processing module;
(d) wherein said mobile post processing module is configured for being worn by the patient while said neural data is being collected; and
(e) wherein said mobile post processing module is configured for performing feature extraction and compression on said neural data and wirelessly transmitting neural information to a remote computer-enabled electronic device configured for viewing, storing, and/or manipulating said neural information.

23. A wireless wearable brain machine interface apparatus, comprising:
(a) an implant recording and transmitting module configured for connection to a plurality of electrodes implant on a patient's cranium, said implant recording and transmitting module comprising:
  (i) a power coil and rectification circuit configured for receiving power from an inductively coupled power source;
  (ii) multiple N-channel recorders configured for storing neural data from a plurality of electrodes coupled to each of said N-channel recorders, which sample neural signals at a sampling rate and convert neural levels though analog-to-digital converters (ADCs) to generate multiple digitized recording outputs;
  (iii) at least one multiplexor configured for multiplexing neural data signals from a number of said N-channel recorders into a single bit stream;
  (iv) at least one modulator configured for converting each single bit stream from a multiplexor by modulating a carrier frequency with each said single bit stream into a wireless digital radio frequency signal for transmission through a radiating element;
(b) a wearable receiving and forwarding module configured for being wearably retained, and not implanted, near the patient's cranium proximal to said implant recording and transmitting module, said wearable receiving and forwarding module including:
  (i) a power generation circuit configured for powering an inductive power coil as the inductively coupled power source to the power coil of said implant recording and transmitting module;
  (ii) a radiator or antenna configured for receiving said radio frequency signal from said implant recording and transmitting module;
  (iii) a demodulator configured for extracting each said single bit stream of neural data from said wireless radio frequency signal;
(c) a mobile post processing module configured for receiving at least one of said single bit stream and performing post-processing of the neural data in response to programming executing on a computer processor within said mobile post processing module;
(d) wherein said mobile post processing module is configured for being worn by the patient while said neural data is being collected; and
(e) wherein said mobile post processing module is configured for performing feature extraction and compression on said neural data and wirelessly transmitting neural information to a remote computer-enabled electronic device configured for viewing, storing, and/or manipulating said neural information.

* * * * *